United States Patent [19]

Birchall et al.

[11] 4,012,513

[45] Mar. 15, 1977

[54] INDOLE DERIVATIVES FOR PROVIDING ANALGESIC AND ANTI-INFLAMMATORY EFFECTS

[75] Inventors: George Richard Birchall, Victoria, Australia; Walter Hepworth; Stephen Collyer Smith, both of Macclesfield, England

[73] Assignee: Imperial Chemical Industries Limited, London, England

[22] Filed: Dec. 23, 1974

[21] Appl. No.: 535,839

Related U.S. Application Data

[63] Continuation-in-part of Ser. No. 296,202, Oct. 10, 1972, Pat. No. 3,884,919.

[30] Foreign Application Priority Data

| | | |
|---|---|---|
| Nov. 3, 1971 | United Kingdom | 51086/71 |
| Apr. 19, 1972 | United Kingdom | 18116/72 |
| June 30, 1972 | United Kingdom | 30767/72 |

[52] U.S. Cl. .............................................. 424/251

[51] Int. Cl.$^2$ ...................................... A61K 31/505

[58] Field of Search .................................... 424/251

[56] References Cited

UNITED STATES PATENTS 3,190,889 6/1965 Shen ........................... 260/256.4 N

*Primary Examiner*—Stanley J. Friedman
*Attorney, Agent, or Firm*—Cushman, Darby & Cushman

[57] ABSTRACT

1-(Heterocyclic)-indol-3-ylacetic acid derivatives, processes for their preparation, and pharmaceutical compositions comprising them. An illustrative compound of the invention is 1-(7-chloroquinazolin-4-yl)-5-methoxy-2-methylindol-3-ylacetic acid. The compounds have anti-inflammatory, analgesic and antipyretic activity.

8 Claims, No Drawings

INDOLE DERIVATIVES FOR PROVIDING ANALGESIC AND ANTI-INFLAMMATORY EFFECTS

This application is a continuation-in-part of Ser. No. 296,202, filed Oct. 10, 1972, now U.S. Pat. No. 3,884,919.

This invention relates to indole derivatives and more particularly it relates to new heterocyclic-indol-3-yl-carboxylic acid derivatives which possess anti-inflammatory, analgesic and antipyretic activity.

According to the invention there are provided compounds of the formula:

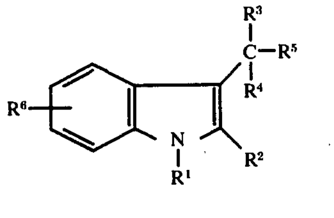

I wherein $R^1$ stands for a heterocyclic radical selected from pyrimidinyl, quinolyl, isoquinolyl, cinnolinyl, quinazolinyl, quinoxalinyl, benzthiazolyl and benzoxazolyl radicals, the said heterocyclic radical being linked to the nitrogen atom of the indole nucleus through a ring carbon atom which is conjugated with a ring nitrogen atom in the said heterocyclic radical, and the said heterocyclic radical optionally bearing not more than two substituents selected from $C_{1-5}$-alkyl, $C_{1-5}$-alkoxy, $C_{1-5}$-alkylthio, amino ($-NH_2$), halogen, trifluoromethyl, trichloromethyl and phenyl substituents; and $R^2$ stands for hydrogen or a $C_{1-3}$-alkyl radical; and $R^3$ and $R^4$, which may be the same or different, stand for hydrogen or a methyl radical; and $R^5$ stands for a radical of the formula $-COR^7$ or $-CH_2OR^8$, wherein $R^7$ stands for a hydroxy, $C_{1-5}$-alkoxy, benzyloxy, phenoxy, di-$C_{1-5}$-alkylamino-$C_{1-5}$alkoxy, ($C_{3-6}$-cycloalkyl)methoxy, amino, $C_{1-5}$-alkylamino, di-$C_{1-5}$-alkylamino, anilino, hydrazino or N-1,3-dicyclohexylureido radical, and $R^8$ stands for hydrogen or a $C_{1-6}$-alkanoyl radical; and $R^6$ stands for hydrogen or a methylenedioxy or ethylenedioxy radical or not more than two substituents selected from $C_{1-5}$-alkoxy, $C_{1-5}$-alkyl, cycloalkyl of not more than 5 carbon atoms, and di-$C_{1-5}$-alkylamino radicals and halogen atoms; and pharmaceutically-acceptable salts thereof.

As stated above, the heterocyclic radical $R^1$ is linked to the nitrogen atom of the indole nucleus through one of its ring carbon atoms which is conjugated with a ring nitrogen atom. Accordingly, it is to be understood that $R^1$ is linked to the nitrogen atom of the indole nucleus through one of the following positions of the former:

when $R^1$ stands for a pyrimidinyl radical, through position 2, 4 or 6 thereof;

when $R^1$ stands for a benzthiazolyl or benzoxazolyl radical, through position 2 thereof;

when $R^1$ stands for a quinolyl or quinazolinyl radical, through position 2 or 4 thereof;

when $R^1$ stands for the cinnolinyl radical, through position 4 thereof;

when $R^1$ stands for a quinoxalinyl radical, through position 2 or 3 thereof; and when $R^1$ stands for an isoquinolyl radical, through position 1 thereof.

It will be appreciated by those skilled in the art that some of the compounds of the formula I possess at least one asymmetric carbon atom, for example this is the case if $R^3$ and $R^4$ are different. These asymmetric compounds may be resolved into the corresponding optically-active forms (i.e. enantiomorphic forms) by conventional procedures. It is to be understood that the racemates of the formula I possess anti-inflammatory, analgesic and antipyretic activity and that, in addition, at least some of the optically active compounds of the formula I possess anti-inflammatory, analgesic and/or antipyretic activity. It is also to be understood that the compounds of this invention encompass both those compounds of the formula I which are racemates and the optically active compounds of the formula I which possess anti-inflammatory, analgesic and/or antipyretic activity.

The substituent(s) which may optionally be present in the heterocyclic radical $R^1$ may, for example, be selected from methyl, ethyl, isopropyl, methoxy, methylthio, amino, fluoro, chloro, bromo, trifluoromethyl, trichloromethyl and phenyl substituents.

A suitable value for $R^2$ when it stands for a $C_{1-3}$-alkyl radical is, for example, a methyl radical.

A suitable value for $R^6$ is, for example, hydrogen or a methylenedioxy or ethylenedioxy radical or not more than two substituents selected from methoxy, ethoxy, propoxy, methyl, ethyl, propyl, butyl and dimethylamino radicals and fluorine, chlorine and bromine atoms.

A suitable value for $R^7$ is, for example, a hydroxy, methoxy, ethoxy, propoxy, butoxy, 2-dimethylaminoethoxy, benzyloxy, phenoxy, cyclohexylmethoxy, amino, methylamino, dimethylamino, anilino, hydrazino or N-1,3-dicyclohexylureido radical.

A suitable value for $R^8$ is, for example, hydrogen or a formyl, acetyl or propionyl radical. Thus, it is to be noted that for convenience in this specification the expression "alkanoyl radical" includes a formyl radical.

Suitable salts of the invention in the case where the compound of the formula I is sufficiently basic are pharmaceutically-acceptable acid-addition salts, for example a hydrochloride, hydrobromide or citrate. A suitable salt in the case where $R^7$ stands for a hydroxy radical is a salt in which the anion is derived from the said compound of the formula I and the cation is a pharmaceutically-acceptable cation, for example an alkali metal, alkaline earth metal, aluminium or ammonium salt, or a salt with a pharmaceutically-acceptable organic base, for example triethanolamine.

Particularly active compound of the invention are 1-(7-chloroquinol-4-yl)-5-methoxy-2-methylindol-3-ylacetic acid, 1-(7-chloroquinazolin-4-yl)-5-methoxy-2-methylindol-3-ylacetic acid, 1-(7-bromoquinazolin-4-yl)-5-methoxy-2-methylindol-3-ylacetic acid, 1-(7-fluoroquinazolin-4-yl)-5-methoxy-2-methylindol-3-ylacetic acid, 5-methoxy-2-methyl-1-(2-methylquinazolin-4-yl)indol-3-ylacetic acid, 1-(7-chlorocinnolin-4-yl)-5-methoxy-2-methylindol-3-ylacetic acid, 1-(7-chloroquinazolin-4-yl)-2,5-dimethylindol-3-ylacetic acid, 1-(2,6-dimethoxypyrimidin-4-yl)-2,5-dimethylindol-3-ylacetic acid, 1-(7-chloroquinazolin-4-yl)-5-fluoro-2-methylindol-3-ylacetic acid, methyl-1-(7-chloroquinazolin-4-yl)-5-methoxy-2-methylindol-3-ylacetate and methyl 1-(7-chloroquinol-4-yl)-5-methoxy-2-methylindol-3-ylacetate, and pharmaceutically-acceptable salts thereof.

According to a further feature of the invention there is provided a process for the manufacture of the compounds of the formula I, wherein $R^1$, $R^2$, $R^3$, $R^4$, $R^5$ and $R^6$ have the meanings stated above except that $R^7$ cannot stand for a hydrazino radical, and pharmaceutically-acceptable salts thereof, which comprises reacting a compound of the formula:

II

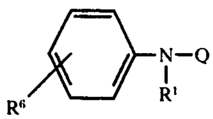

wherein $R^1$ and $R^6$ have the meanings stated above and Q stands for an amino radical ($-NH_2$) or a radical of the formula:

III

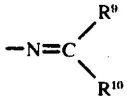

wherein $R^9$ stands for hydrogen or a methyl or ethyl radical, and $R^{10}$ stands for a methyl, ethyl or phenyl radical, or an acid-addition salt thereof, with a compound of the formula:

$$R^2COCH_2CR^3R^4R^5 \quad IV$$

wherein $R^2$, $R^3$, $R^4$ and $R^5$ have the meanings stated immediately above, under the influence of heat.

A suitable acid-addition salt of the compound of the formula II is for example, a hydrochloride, hydrobromide, sulphate or fluoroborate. The reaction may be carried out at, for example, 40° to 150° C., and more particularly 60° to 120° C. The reaction is preferably carried out in the presence of an acid, for example laevulinic acid (which is, of course, within the definition of the reactant of formula IV), acetic acid, or a relative strong acid, for example hydrochloric, sulphuric, perchloric or polyphosphoric acid. Under these conditions the reaction may optionaly be carried out in a suitable solvent, for example water, a $C_{1-4}$ alkanol, for example ethanol, or acetic acid, or a mixture of any of these, and/or in an excess of a low melting compound of the formula IV, for example laevulinic acid.

It is to be understood that, when the starting material of the formula IV is a carboxylic acid and a $C_{1-4}$-alkanol is used as a solvent, the product is obtained as the corresponding alkyl ester. Alternatively, the reaction is preferably carried out in the presence of a Lewis acid, for example boron trifluoride ethereate. A $C_{1-4}$-alkanol, for example methanol or ethanol, may optionally also be present, but in this case when the starting material of the formula IV is a carboxylic acid, the product is obtained as the corresponding alkyl ester.

Those of the starting materials of the formula II which are hydrazine may be obtained by reacting the appropriate phenylhydrazine of the formula:

V

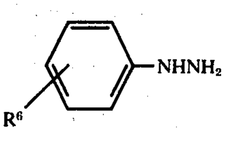

wherein $R^6$ has the meaning stated above, with a compound of the formula $R^1Hal$, wherein $R^1$ has the meaning stated above and Hal stands for a chlorine, bromine or iodine atom, in the presence of sodium acetate or a hydrate thereof, in the presence of a solvent, for example water, a $C_{1-4}$-alkanol, benzene or 1,2-dimethoxyethane. The remaining starting materials, that is, the hydrazones of the formula II, may be obtained by reacting the appropriate hydrazine of the formula II with the appropriate aldehyde or ketone of the formula $R^9COR^{10}$, wherein $R^9$ and $R^{10}$ have the meanings stated above. This reaction may be carried out in an excess of the said aldehyde or ketone and/or in the presence of an organic solvent, for example benzene or toluene. The reaction may optionally be catalysed by means of an inorganic or organic acid, for example sulphuric or acetic acid. However, a preferred method of making those of the said hydrazones wherein $R^1$ stands for a quinazolinyl or cinnolinyl radical comprises reacting a compound of the formula:

VI

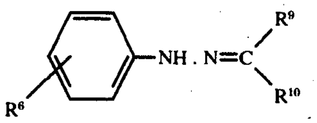

with a compound of the formula $R^1Hal$, under the influence of heat, for example under reflux, and in a dry organic solvent, for example 1,2-dimethoxyethane, and wherein $R^6$, $R^9$, $R^{10}$ and Hal have the meanings stated above and $R^1$ has the meaning stated immediately above.

According to a further feature of the invention there is provided a process for the manufacture of those of the compounds of the formula I wherein $R^1$, $R^2$, $R^3$, $R^4$ and $R^6$ have the meanings stated above, and $R^5$ stands for a carboxy radical, and pharmaceutically-acceptable salts thereof, which comprises hydrolysing the corresponding compound of the formula:

VII

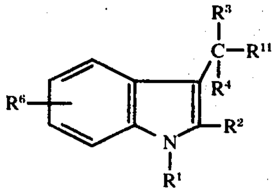

wherein $R^1$, $R^2$, $R^3$, $R^4$ and $R^6$ have the meanings stated above, and $R^{11}$ stands for a cyano, carbamoyl, alkoxycarbonyl, benzyloxycarbonyl or phenoxycarbonyl radical.

A suitable hydrolytic agent is, for example, an alkali metal hydroxide, for example sodium hydroxide or potassium hydroxide. The hydrolysis is carried out in the presence of water, and optionally an organic solvent, for example a $C_{1-4}$-alkanol, for example ethanol, may be present. The reaction may optionally be accelerated or completed by the application of heat, for example it may be carried out at 50° to 150° C., for example at reflux temperature.

Those of the starting materials of the formula VII wherein $R^{11}$ stands for a cyano radical, $R^3$ and $R^4$ stand for hydrogen, and $R^1$, $R^2$ and $R^6$ have the meanings stated above, may be obtained by the following sequence of reactions:

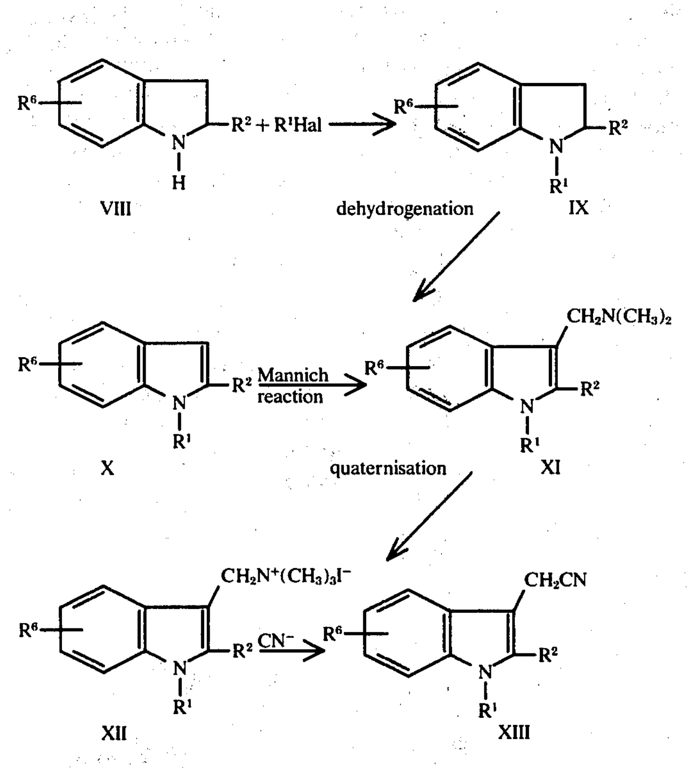

VIII IX X XI XII XIII

The amide starting materials of the formula VII (i.e. wherein $R^{11}$ stands for a carbamoyl radical) are formed as a by-product in the production of the nitriles of the formula XIII when made by the above sequence of reactions, and they may be obtained from the latter compounds by hydrolysis. The ester starting materials of the formula VII are obtainable by a process described hereinbefore.

According to a further feature of the invention there is provided a process for the manufacture of the compounds of the formula I, wherein $R^1$, $R^2$, $R^3$, $R^4$ and $R^6$ have the meanings stated above and $R^5$ stands for a radical of the formula —$COR^7$ or $CH_2OR^8$, wherein $R^7$ has the meaning stated above and $R^8$ stands for a $C_{2-6}$-alkanoyl radical, and pharmaceutically-acceptable salts thereof, which comprises dehydrogenating the corresponding indoline derivative of the formula:

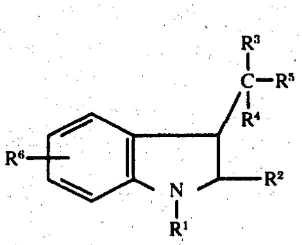

XIV wherein $R^1$, $R^2$, $R^3$, $R^4$ and $R^6$ have the meanings stated above, and $R^5$ has the meaning stated immediately above.

It is to be understood that by the word "dehydrogenating" there is meant the removal of one hydrogen atom from the 2-position, and one from the 3-position, of the said indoline derivative, so as to give the corresponding indole derivative. The dehydrogenation may be effected by means of a dehydrogenation catalyst, for example a palladium on charcoal catalyst, in the presence of a suitable organic solvent, for example diphenyl ether, at an elevated temperature, for example at or about reflux temperature. Alternatively, the dehydrogenation may be effected by means of a known compound having dehydrogenating properties, for example 2,3,5,6-tetrachloro-1,4-benzoquinone or 2,3-dichloro-5,6-dicyano-1,4-benzoquinone, in a suitable solvent, for example dry xylene, 1,2-dimethoxyethane or dimethylformamide, at 20° to 160° C., for example at reflux temperature.

The indoline starting materials of the formula XIV, except for the hydrazides wherein $R^5$ stands for the group —$CONHNH_2$, may be obtained by using an analogous process to that outlined above for the production of the intermediates of the formula IX. The said hydrazides may be obtained by interaction of an appropriate ester of the formula XIV with hydrazine, by an analogous reaction to that described below.

According to a further feature of the invention there is provided a process for the manufacture of those of the compounds of the formula I wherein $R^1$, $R^2$, $R^3$, $R^4$ and $R^6$ have the meanings stated above, and $R^5$ stands for a radical of the formula —$COR^7$ wherein $R^7$ stands for a $C_{1-5}$-alkoxy, benzyloxy, di-$C_{1-5}$-alkylamino-$C_{1-5}$-alkoxy or ($C_{3-6}$-cycloalkyl)methoxy radical, and pharmaceutically-acceptable salts thereof, which comprises esterifying the corresponding carboxylic acid of the formula I wherein $R^5$ stands for a carboxy radical, or a salt, acid halide or anhydride thereof.

The said esterification may be carried out by any appropriate general method, for example:

(1) By reacting the said carboxylic acid with the alcohol reactant, which may optionally be present in excess, in the presence of an acid, for example a Lewis acid, for example boron trifluoride etherate, or sulphuric acid (this is not suitable in the case where $R^1$ stands for a quinazolinyl or cinnolinyl radical). This reaction may conveniently be carried out at about 40° to 120° C., for example under reflux.

(2) By reacting an acid halide, for example an acid chloride, or an acid anhydride (which expression includes a mixed acid anhydride) with the alcohol reactant. The reaction may be carried out in an excess of the alcohol reactant and/or in the presence of an organic solvent, for example chloroform, dimethylformamide, acetonitrile, tetrahydrofuran or 1,2-dimethoxyethane, and preferably the said alcohol reactant or organic solvent is used in a dry form. This reaction may conveniently be carried out at about 20° to 100° C., for example under reflux.

(3) By reacting the said carboxylic acid with a carbodiimide, for example dicyclohexylcarbodiimide, and then, without isolation, reacting the product with the alcohol reactant. The reaction may be carried out in the presence of an organic solvent, for example chloroform, 1,2-dimethoxyethane, dimethylformamide, acetonitrile or tetrahydrofuran, and preferably the solvent is used in dry form. The reaction may conveniently be carried out at about 20° to 100° C., preferably at room temperature.

(4) By reacting a metal salt, for example a sodium salt, of the said carboxylic acid with a compound of the formula $R^7X$, which may optionally be in excess, wherein $R^7$ stands for a $C_{1-5}$-alkyl, benzyl, di-$C_{1-5}$-alkylamino-$C_{1-5}$-alkyl or ($C_{3-6}$-cycloalkyl)methyl radical, and X stands for a halogen atom, for example a chlorine, bromine or iodine atom, or a toluenesulphonyloxy or methanesulphonyloxy radical. The reaction may be carried out in the presence of an organic solvent, for example dimethylformamide, 1,2-dimethoxyethane, acetonitrile or tetrahydrofuran, and preferably the solvent is used in dry form. The reaction may conveniently be carried out at about 20° to 100° C. for example at room temperature.

According to a further feature of the invention there is provided a process for the manufacture of the compounds of the formula I, wherein $R^1$ stands for a quinazolinyl, cinnolinyl, benzoxazolyl or benzthiazolyl radical, which is linked to the nitrogen atom of the indole nucleus through a ring carbon atom which is conjugated with a ring nitrogen atom in said radical, and which may optionally be substituted as stated above, and $R^5$ stands for a radical of the formula $—COR^8$ or $—CH_2OR^8$, wherein $R^7$ stands for a $C_{1-5}$-alkoxy, benzyloxy, phenoxy, di-$C_{1-5}$-alkylamino-$C_{1-5}$-alkoxy or ($C_{3-6}$-cycloalkyl)methoxy radical and $R^8$ stands for a $C_{2-6}$-alkanoyl radical, and $R^2$, $R^3$, $R^4$ and $R^6$ have the meanings stated above, and pharmaceutically-acceptable salts thereof, which comprises reacting a compound of the formula:

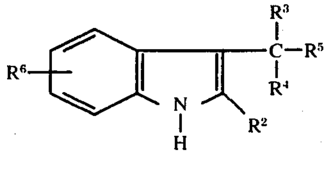

XV with a halogenoheterocyclic compound of the formula $R^1Hal$, wherein $R^1$ and $R^5$ have the meanings stated immediately above and $R^2$, $R^3$, $R^4$, $R^6$ and Hal have the meanings stated above, in the presence of sodium or potassium or the hydride or amide thereof or n-butyllithium or lithium di-isopropylamide.

The process is conveniently carried out in a dry inert solvent, for example dimethylformamide or hexamethylenephosphorus triamide, and at about 20 to 50° C.

The starting materials of the formula XV may be obtained by conventional procedures involving the acid-catalysed reaction of a compound of the formula IV with an appropriate compound of the formula II.

According to a further feature of the invention there is provided a process for the manufacture of the compounds of the formula I wherein $R^1$ stands for a quinazolinyl or cinnolinyl radical, which is linked to the nitrogen atom of the indole nucleus through a ring carbon atom which is conjugated with a ring nitrogen atom in said radical, and which may optionally be substituted as stated above, and $R^5$ stands for a radical of the formula $—COR^7$ or $—CH_2OR^8$, wherein $R^7$ stands for a $C_{1-5}$-alkoxy, benzyloxy, phenoxy, di-$C_{1-5}$-alkylamino-$C_{1-5}$-alkoxy, ($C_{3-6}$-cycloalkyl)methoxy, amino, $C_{1-5}$-alkylamino, di-$C_{1-5}$-alkylamino, anilino or N-1,3-dicyclohexylureido radical and $R^8$ stands for a $C_{2-6}$-alkanoyl radical, and $R^2$, $R^3$, $R^4$ and $R^6$ have the meanings stated above, and pharmaceutically-acceptable salts thereof, which comprises reacting a compound of the formula:

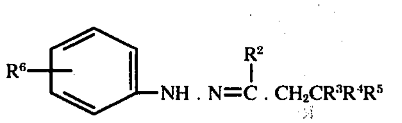

XVI with a compound of the formula $R^1Y$, so as to give a compound of the formula:

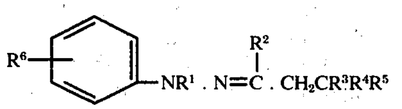

XVII and then ring-closing the said compound of the formula XVII so as to give the desired product of the formula I, and wherein $R^1$ and $R^5$ have the meanings stated immediately above, $R^2$, $R^3$, $R^4$ and $R^6$ have the meanings stated above, and Y stands for a chlorine, bromine or iodine atom or a phenoxy radical.

The entire process is conveniently carried out in a dry, relatively high boiling, inert organic solvent, for example such a solvent of boiling point 50° to 200° C., for example 1,2-dimethoxyethane, diethyleneglycol dimethyl ether, dioxan, diphenyl ether or dimethylformamide. The first stage of the process is conveniently carried out at 20° to 100° C., and more particularly at about 60° to 80° C. The ring-closure step is carried out by heating the product of the formula XVII to elevated temperature, for example 40° to 150° C., for example reflux temperature, preferably under acidic conditions. Suitable acidic conditions are provided by the presence of the hydrogen halide HHal which is one product of the first stage of the process, i.e. the conversion of XVI into XVII. Alternatively, if desired, a relatively strong acid, for example hydrochloric, sulphuric, perchloric or polyphosphoric acid, or a Lewis acid, for example boron trifluoride etherate in the presence of an inert organic solvent, for example diethyl ether or tetrahydrofuran, or laevulinic or acetic acid, may be added to the reaction mixture.

The starting materials of the formula XVI may be obtained by reacting a phenylhydrazine derivative of the formula V, wherein $R^6$ has the meaning stated above, with a compound of the formula IV, wherein $R^2$, $R^3$, $R^4$ and $R^5$ have the meanings stated immediately above. The reaction may be carried out at 0° to 100° C., and more particularly at 25° to 50° C., and in a suitable organic solvent, for example a $C_{1-4}$-alkanol, for example ethanol, or benzene, 1,2-dimethoxyethane, or diethyl ether. A catalytic quantity of an acid, for example acetic, sulphuric or perchloric acid, may optionally also be present.

According to a further feature of the invention there is provided a process for the manufacture of compounds of the formula I, wherein $R^1$, $R^2$, $R^3$, $R^4$ and $R^6$ have the meanings stated above and $R^5$ stands for a radical of the formula —$COR^7$, wherein $R^7$ stands for an amino, $C_{1-5}$-alkylamino, di-$C_{1-5}$-alkylamino, anilino or hydrazino radical, and pharmaceutically-acceptable salts thereof, which comprises carrying out a known general process for making amides using as starting material a carboxylic acid of the formula I wherein $R^5$ stands for a carboxy radical, or an acid halide, anhydride or nitrile thereof, so as to obtain the desired product.

The said amides may be obtained, for example, as follows:

(1) By reacting an appropriate ester, for example an ester of the formula I wherein $R^5$ stands for an alkoxycarbonyl radical, or an acid halide or anhydride (which term includes a mixed acid anhydride) with a reactant of the formula $R^7H$, wherein $R^7$ has the meaning stated immediately above. The process may be carried out in the presence of an organic solvent, for example dimethylformamide, chloroform, acetonitrile, tetrahydrofuran or 1,2-dimethoxyethane. In the case where $R^5$ stands for an alkoxycarbonyl radical, but not in the other cases, the solvent may be a $C_{1-4}$-alkanol. In the case where the reactant is an acid halide or anhydride, the solvent is preferably used in dry form. The process may be carried out at 20° to 100° C.; in the case where the reactant is an ester it is preferably carried out under reflux, but in the other cases it is preferably carried out at about room temperature.

(2) By reacting the said carboxylic acid with a carbodiimide, for example dicyclohexylcarbodiimide, and then reacting the product with the reactant of the formula $R^7H$, wherein $R^7$ has the meaning stated immediately above. The process is conveniently carried out in a dry organic solvent, for example dimethylformamide, tetrahydrofuran, chloroform, acetonitrile or 1,2-dimethoxyethane, at 20° to 100° C., preferably at room temperature.

According to a further feature of the invention there is provided a process for the manufacture of those of the compounds of the formula I wherein $R^1$, $R^2$, $R^3$, $R^4$ and $R^6$ have the meanings stated above and $R^5$ stands for a radical of the formula —$COR^7$ wherein $R^7$ stands for a N-1,3-dicyclohexylureido radical, and pharmaceutically-acceptable salts thereof, which comprises reacting the corresponding carboxylic acid of the formula I, wherein $R^5$ stands for a carboxy radical, with dicyclohexylcarbodiimide in a suitable organic solvent.

A suitable solvent is, for example, 1,2-dimethoxyethane, and the process is conveniently carried out at room temperature.

According to a further feature of the invention there is provided a process for the manufacture of those of the compounds of formula I wherein $R^1$ contains one or two $C_{1-5}$-alkoxy substituents, $R^2$, $R^3$, $R^4$ and $R^6$ have the meanings stated above, and $R^5$ stands for a carboxy or hydroxymethyl radical, and pharmaceutically-acceptable salts thereof, which comprises reacting the corresponding compound of the formula I, wherein $R^1$ contains one or two active halogen substituents, with an alkali metal derivative of a $C_{1-5}$-alkanol.

By an "active halogen substituent" we mean a halogen substituent which, because of its chemical nature, its position in the said heterocyclic radical $R^1$, and the chemical nature of said heterocyclic radical itself, is sufficiently active to take part in standard nucleophilic displacement reactions. Two examples of such active halogen substituents are the chlorine substituents in a 2,6-dichloropyrimid-4-yl radical. The reaction may be carried out in an organic solvent, which can be the alkanol corresponding to the alkali metal alkoxide used as reactant. The reaction is conveniently carried out at 60° to 120° C., for example under reflux.

According to a further feature of the invention there is provided a process for the manufacture of those of the compounds of the formula I wherein $R^1$, $R^2$, $R^3$, $R^4$ and $R^5$ have the meanings stated above, and $R^6$ stands for a $C_{1-5}$-alkoxy radical optionally together with $C_{1-5}$-alkyl, cycloalkyl of not more than 5 carbon atoms, di-$C_{1-5}$-alkylamino or halogeno substituent, and pharmaceutically-acceptable salts thereof, which comprises reacting the corresponding compound of the formula I, wherein $R^6$ stands for a hydroxy radical, optionally together with an additional substituent as stated immediately above, or the corresponding alkali metal derivative (i.e. wherein an alkali metal atom replaces the hydrogen atom of the said hydroxy radical), with a compound of the formula $R^{12}X$, wherein $R^{12}$ stands for a $C_{1-5}$-alkyl radical and X has the meaning stated above, and, in the case where the hydroxy derivative is used as reactant, in the presence of an acid-binding agent.

A suitable acid-binding agent is sodium or potassium hydride, or sodium or potassium carbonate. The reaction is conveniently carried out in a dry organic solvent, for example acetone, dimethylformamide, 1,2-dimethoxyethane or tetrahydrofuran.

The hydroxy derivatives used as starting material may be obtained by the debenzylation of the corresponding benzyloxy derivatives, either by hydrogenolysis, for example with hydrogen and a 10%w/w palladium on charcoal catalyst, or using a solution of hydrogen bromide in glacial acetic acid at 0° to 20° C.

According to a further feature of the invention there is provided a process for the manufacture of those of the compounds of the formula I wherein $R^1$ bears a fluorine, chlorine or bromine substituent and $R^2$, $R^3$, $R^4$, $R^5$ and $R^6$ have the meanings stated above, apart from the case where $R^7$ stands for a hydrazino radical, and pharmaceutically-acceptable salts thereof, which comprises diazotising the corresponding compound of the formula I wherein $R^1$ bears an amino substituent, and then, in the case of the chloro or bromo substituent, reacting the diazonium salt with a solution of cuprous chloride or bromide in hydrochloric or hydrobromic acid respectively at 10° to 40° C., or, in the case of the fluoro substituent, thermally decomposing the dry diazonium fluoroborate salt at 40°–100° C.

The diazotisation is carried out in conventional manner at a relatively low temperature, for example 0° to 5° C. In the case of the chloro or bromo substituent, the second stage of the process is conveniently carried out at room temperature.

The amino derivatives used as starting materials may be obtained by reducing the corresponding nitro derivatives by means of hydrogen and a hydrogenation catalyst, for example a palladium on charcoal catalyst, and the nitro derivatives themselves may be obtained by the first process described herein.

According to a further feature of the invention there is provided a process for the manufacture of those of the compounds of the formula I wherein $R^1$, $R^2$, $R^3$, $R^4$ and $R^6$ have the meanings stated above, and $R^5$ stands for a hydroxymethyl radical, and pharmaceutically-acceptable salts thereof, which comprises reacting a corresponding ester of the formula I, wherein $R^5$ stands for an alkoxycarbonyl, aralkoxycarbonyl or aryloxycarbonyl radical, with sodium borohydride, potassium borohydride or lithium aluminium hydride.

In the case of sodium or potassium borohydride, the reaction may be carried out in an organic solvent, for example a $C_{1-4}$-alkanol, for example methanol, and at a temperature of 20° to 120° C., for example under reflux. In the case of lithium aluminium hydride, a suitable solvent is dry tetrahydrofuran or ether. The esters used as starting materials may be obtained by methods described hereinbefore.

According to a further feature of the invention there is provided a process for the manufacture of those of the compounds of the formula I wherein $R^1$, $R^2$, $R^3$, $R^4$ and $R^6$ have the meanings stated above and $R^5$ stands for a radical of the formula $-CH_2OR^8$, wherein $R^8$ stands for a $C_{1-6}$-alkanoyl radical, and pharmaceutically-acceptable salts thereof, which comprises acylating the corresponding compounds of the formula I wherein $R^5$ stands for a hydroxymethyl radical.

The acylation may be carried out in conventional manner, for example, in the case where $R^8$ stands for a $C_{2-6}$-alkanoyl radical, the acylation may be carried out by reacting the said hydroxy derivative with an acid halide or anhydride, for example acetic anhydride, optionally in the presence of an organic solvent. The reaction may be accelerated or completed by the application of heat. In the case where $R^8$ stands for a formyl radical, the acylation may be carried out, for example, by reacting the said hydroxy derivative with a $C_{1-3}$-alkyl formate, for example ethyl formate, which alkyl formate may optionally be present in excess, in the presence of a catalytic amount of an acid, for example sulphuric acid or a Lewis acid. Alternatively, the formates may be obtained by reacting the said hydroxy derivative with formic acid. Both formylation reactions may be accelerated or completed by the application of heat.

The pharmaceutically-acceptable salts of the invention are obtained by conventional procedures.

The anti-inflammatory activity of the compounds of the invention has been demonstrated in two well known tests involving adjuvant induced arthritis and carrageenin induced oedema in the rat, their analgesic activity has been demonstrated in the socalled mouse squirm test and in another test involving established arthritis in rats, and their antipyretic activity has been demonstrated in a standard antipyretic test in rats. The activity in these tests depends upon the chemical structure of the particular compound being tested, but generally speaking the compounds of this invention show activity at a dose in the region 0.5 to 100mg./kg. No toxic effect or undesirable side effects have been observed in the rat or mouse with the compounds of the invention, at doses at which the compounds show activity in the above-mentioned tests.

When a compound of the invention is used as an anti-inflammatory, analgesic or antipyretic agent in the treatment of warm-blooded mammals, for example man, for example for the treatment of rheumatoid arthritis, it is recommended that said compound be administered orally at a total daily dose of 25 to 1000mg. per 70kg. bodyweight, for example as an aqueous or nonaqueous solution or suspension or as a dosage unit form, for example a tablet or capsule comprising 5 to 250mg. of the said compound. Alternatively, the said compound may be dosed rectally as a suppository at a total daily dose of 25 to 1000mg. per 70kg. bodyweight, or it may be administered topically as necessary.

According to a further feature of the invention there are provided pharmaceutical compositions comprising a compound of the formula I, wherein $R^1$, $R^2$, $R^3$, $R^4$, $R^5$ and $R^6$ have the meanings stated above, or a pharmaceutically-acceptable salt thereof, and an inert pharmaceutically-acceptable diluent or carrier.

The said pharmaceutical compositions may be in the form of, for example, dosage unit forms, for example tablets or capsules, or suppositories, aqueous or non-aqueous solutions or suspensions, sterile injectable aqueous or non-aqueous solutions, creams, lotions or ointments. The compositions are obtainable in a conventional manner using conventional diluents and carriers.

The pharmaceutical compositions of the invention may contain, in addition to a compound of the invention, at least one known agent having anti-inflammatory and/or analgesic activity, for example aspirin, paracetamol, codeine, chloroquine, phenylbutazone, oxyphenbutazone, indomethacin, mefenamic acid, flufenamic acid, ibufenac, or an anti-inflammatory steroid, for example prednisolone. Those compositions intended for oral administration may, in addition, optionally contain at least one antacid, for example aluminium hydroxide, and/or a uricosuric agent, for example probenecid.

The invention is illustrated by the following non-limiting Examples:

EXAMPLE 1

N-Phenyl-N-(2-amino-6-methylpyrimidin-4-y)hydrazine (7g.) was suspended in laevulinic acid (25g.), and the mixture was heated at 100° C. for 1 hour whilst a stream of dry hydrogen chloride was passed through it. The mixture was then heated for a further 5 hours at 100° C. and, after cooling, it was diluted with ethyl acetate (150ml.). The resulting precipitate was collected by filtration and washed with ether (150ml.). The solid was suspended in hot water (150ml.; ca 70° C.), and aqueous ammonium hydroxide (D= 0.880) was added until the pH of the solution was 10. The resulting mixture was filtered, and, whilst it was still hot, the filtrate carefully acidified with glacial acetic acid until no further precipitate was obtained. The mixture was cooled to room temperature and then filtered. The solid residue was added to methanol (100ml.), the mixture heated under reflux for 30 minutes, and then cooled and filtered. The solid residue was crystallised from methanol (300ml.), and there was thus obtained 1-(2-amino-6-methylpyrimidin-4-yl)-2-methylindol-3-ylacetic acid, m.p. 154°–155° C. (decomposition).

The hydrazine derivative used as starting material was obtained as follows:

A mixture of phenylhydrazine (66ml.), 2-amino-4-chloro-6-methylpyrimidine (86g.), and sodium acetate trihydrate (120g.) in water (2 l.) was heated under reflux for 16 hours. The mixture was cooled, and adjusted to pH 9.0 by the addition of 40% w/v aqueous sodium hydroxide. The resulting precipitate was collected by filtration, and washed successively with water (2 l.) and ethanol (200ml.). The solid was crystallised from ethanol to give N-phenyl-N-(2-amino-6-methylpyrimidin-4-yl)hydrazine, m.p. 173°–174° C.

EXAMPLE 2

A mixture of N-phenyl-N-(2,6-dichloropyrimidin-4-yl)hydrazine (30g.) and laevulinic acid (50g.) was heated at 100° C. for 3 hours whilst a stream of hydrogen chloride gas was passed through it. The mixture was cooled and added to water (400ml.), and the resulting mixture filtered to give 1-(2,6-dichloropyrimidin-4-yl)-2-methylindol-3-ylacetic acid, m.p. 205°–207° C.

The hydrazine derivative used as starting material was prepared as follows:

A mixture of 2,4,6-trichloropyrimidine (50ml.) and phenylhydrazine (45ml.) was added to a solution of sodium acetate trihydrate (100g.) in water (270ml.) and ethanol (720ml.). The resulting mixture was kept at room temperature for 3 days. The resulting crystalline precipitate was collected by filtration, washed with ethanol (100ml.) and dried at 60° C. to give N-phenyl-N-(2,6-dichloropyrimidin-4-yl)hydrazine, m.p. 114°–116° C.

EXAMPLE 3

A mixture of 2-methyl-1-quinol-4-ylindol-3-ylacetonitrile and 2-methyl-1-quinol-4-ylindol-3-ylacetamide (obtained as described below) was dissolved in ethanol (50ml.). 10% w/v Aqueous potassium hydroxide (50ml.) was added, and the mixture was heated under reflux for 15 hours. The solvents were then evaporated in vacuo, and the residue was diluted with water (100ml.). The aqueous solution was washed with chloroform (3 × 50ml.) and then carefully acidified with 2N-hydrochloric acid to pH 5. The resulting mixture was filtered and the solid residue was washed with water and then dried at 60° C. There was thus obtained 2-methyl-1-quinol-4-ylindol-3-ylacetic acid, m.p. 235°–240° C.

The mixture of nitrile and amide used as starting material was obtained as follows:

A solution of 2-methylindoline (3.96g.) and 4,7-dichloroquinoline (5.91g.) in ethanol (100ml.) containing one drop of concentrated hydrochloric acid was heated under reflux for 4 hours. The solution was cooled, and to it was added a saturated solution of sodium acetate in ethanol (100ml.), followed by water (200ml.). The mixture was extracted with chloroform (2 × 50ml.), and the combined extracts were dried ($MgSO_4$) and evaporated to give 7-chloro-4-(2-methylindolin-1-yl)quinoline as a yellow oil [the corresponding hydrochloride was obtained in conventional manner and had m.p. 248°–250° C. (decomposition)].

A solution of 7-chloro-4-(2-methylindolin-1-yl)quinoline (17g.) in diphenyl ether (50ml.) containing 10% w/w palladium on charcoal catalyst (6.5g.) was heated under reflux for 3 hours. The mixture was cooled and filtered, and the solid residue was extracted with hot chloroform (3 × 50ml.; ca 60° C.). The chloroform was evaporated in vacuo from the extract. The residue was chromatographed on a column of chromatographic silica gel (column dimensions: 20 × 3.5cm.) using a 1:3 v/v mixture of diethyl ether and petroleum ether (b.p. 40°–60° C.) as eluant. The solvents were evaporated in vacuo from the eluate to give 4-(2-methylindol-1-yl)quinoline, m.p. 78°–80° C.

A solution of 4-(2-methylindol-1-yl)quinoline (6g.) in dioxan (50ml.) was added to 2N-acetic acid (50ml.) containing 37% w/v formalin solution (1.6g.) and 30% w/v aqueous dimethylamine solution (3.2g.). The mixture was heated at 80° C. for 4 hours. A further quantity of 37% w/v formalin solution (1.6g.) and 30% w/v aqueous dimethylamine solution (3.2g.) were then added, and heating was maintained at 80° C. for a further 16 hours. The mixture was then evaporated in vacuo to dryness. 2N-Aqueous potassium hydroxide solution (50ml.) was added to the residue, and the mixture was extracted with chloroform (3 × 50ml.). The combined chloroform extracts were extracted with 4N-hydrochloric acid (3 × 50ml.). The combined acidic extracts were basified with 40% w/v aqueous potassium hydroxide solution, and then extracted with chloroform (3 × 50ml.). The combined chloroform extracts were dried ($MgSO_4$) and evaporated to yield an oil (6.8g.). To a solution of the oil in dry ethanol (50ml.) was added methyl iodide (3ml.), and the solution was stirred at room temperature for 20 hours. The precipitate which formed was filtered off and dried at 60° C. to give N-(1-quinol-4-yl-2-methylindol-3-ylmethyl)trimethylammonium iodide, m.p. 213°–215° C. (decomposition).

A mixture of N-(1-quinol-4-yl-2-methylindol-3-ylmethyl)trimethylammonium iodide (6.5g.), potassium cyanide (10g.), 2-methoxyethanol (50ml.) and water (50ml.) was heated under reflux for 20 hours. The mixture was then cooled and diluted with water (150ml.), and the resulting mixture extracted with ethyl acetate (3 × 50ml.). The combined extracts were dried ($MgSO_4$) and evaporated in vacuo to give a mixture of 2-methyl-1-quinol-4-ylindol-3-ylacetonitrile and 2-methyl-1-quinol-4-ylindol-3-ylacetamide.

EXAMPLE 4

A mixture of ethyl 1-quinazolin-4-ylindolin-3-yl-acetate (2.6g.) and 10% w/w palladium on charcoal catalyst (1.3g.) in diphenyl ether (20ml.) was heated under reflux for 30 minutes. The mixture was cooled to room temperature, mixed with diethyl ether (50ml.) and filtered through diatomaceous earth. The solid residue was washed with diethyl ether (50ml.). The combined diethyl ether solution was evaporated in vacuo, and the residue was chromatographed on silica gel (ca 150g.) using, as eluant, petroleum ether (b.p. 40°–60° C.) containing an increasing proportion of diethyl ether. Diphenyl ether was recovered from the first fractions (rich in petroleum ether). Evaporation in vacuo of later fractions gave a syrup which crystallised from a mixture of diethyl ether and petroleum ether (b.p. 40°–60° C.) to give ethyl 1-quinazolin-4-ylindol-3-ylacetate, m.p. 65°–67° C.

In a similar manner, starting with the appropriate indoline derivative, there were obtained the following compounds:

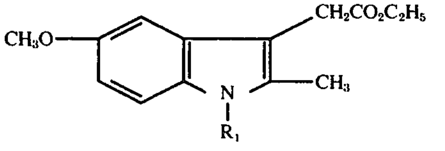

XIII

| $R^1$ | Characteristic Properties |
|---|---|
| quinazolin-4-yl | m.p.121–123° C. |
| benzthiazol-2-yl | m.p.158–160° C. |
| 4-methyl-2-phenylpyrimidin-6-yl | m.p.160–162° C. |
| quinol-4-yl (It should be noted that this product was obtained from the corresponding 7-chloroquinol-4-yl derivative described below; i.e. the 7-chlorine substituent was removed during the reaction.) | NMR: $-OCH_3$, τ6.15 Shown to be pure on thin layer chromatography (TLC) on silica gel; elution with 1:1 v/v ether-petroleum ether, b.p.40–60° C.* |
| quinol-2-yl | NMR: $-OCH_3$, τ6.12 Shown to be pure on TLC (system as above) |

*Hereinafter referred to as system A.

The ethyl 1-quinazolin-4-ylindolin-3-ylacetate used as starting material in this Example was obtained as follows:

A mixture of 4-chloroquinazoline (2.3g.) and ethyl indolin-3-ylacetate (2.6g.) in 1,2-dimethoxyethane (30ml.) was heated under reflux for 15 minutes. The mixture was cooled and filtered, and the solid residue was dissolved in ice-water (40ml.). To the solution was added saturated sodium acetate solution (10ml.), and the mixture was extracted with ethyl acetate (3 × 50ml.). The combined extracts were dried ($Na_2SO_4$), and the solvent evaporated in vacuo to give ethyl 1-quinazolin-4-ylindolin-3-ylacetate as a syrup which was proved to be pure by TLC (system A).

The ethyl 5-methoxy-2-methyl-1-quinazolin-4-yl-indolin-3-ylacetate (m.p. 126°–128° C.) used as starting material was prepared in analogous fashion from ethyl 5-methoxy-2-methylindolin-3-ylacetate.

The ethyl 5-methoxy-2-methyl-1-(4-methyl-2-phenylpyrimidin-6-yl)indolin-3-ylacetate used as starting material in this Example was obtained as follows:

A mixture of ethyl 5-methoxy-2-methylindolin-3-ylacetate (2.0g.), 6-chloro-4-methyl-2-phenylpyrimidine (1.76g.) and concentrated hydrochloric acid (0.5ml.) in ethanol (50ml.) was heated under reflux for 5 hours. The solution was cooled, saturated sodium acetate solution (3ml.) was added, and the mixture was concentrated in vacuo. The residue was diluted with water (30ml.) and extracted with ethyl acetate (3 × 30ml.). The combined exracts were washed with water and then dried ($Na_2SO_4$), and the solvent was evaporated in vacuo at ca 50° C. to give ethyl 5-methoxy-2-methyl-1-(4-methyl-2-phenylpyrimidin-6-yl)indolin-3-ylacetate as a syrup. This was shown to be pure by TLC (System A) and by NMR spectroscopy ($OCH_3$ at 6.23τ).

In a similar manner, starting with the appropriate chloroheterocyclic compound, the following indoline starting materials were obtained:

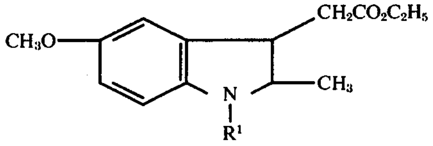

| $R^1$ | Characteristic Properties |
|---|---|
| quinol-2-yl | NMR: $-OCH_3$, τ6.20 Shown to be pure on TLC (System A) |
| 7-chloroquinol-4-yl | NMR: $-OCH_3$, τ6.18 Shown to be pure on TLC (System A) |
| benzthiazol-2-yl | m.p.91–93° C. |

EXAMPLE 5

A mixture of ethyl 1-(7-chloroquinol-4-yl)-5-methoxy-2-methylindolin-3-ylacetate (7.0g.) and 2,3,5,6-tetrachloro-1,4-benzoquinone (5.6g.) in dry xylene (50ml.) was heated under reflux for 1.5 hours. The mixture was then cooled and filtered. The filtrate was washed successively with cold 2N-sodium hydroxide solution (2 × 30ml.) and water (2 × 50ml.). The organic layer was dried ($MgSO_4$) and evaporated in vacuo to dryness, and the residue (dissolved in the minimum volume of diethyl ether) was adsorbed on a column of chromatographic silica gel (column dimensions: 15 × 3.5cm.). The column was eluted with a 1:3 v/v mixture of diethyl ether and petroleum ether (b.p. 40°–60° C.), and the eluate was evaporated in vacuo to give ethyl 1-(7-chloroquinol-4-yl)-5-methoxy-2-methylindol-3-ylacetate as a yellow oil, NMR: $-OCH_3$, τ6.12.

The preparation of the indoline derivative used as starting material is described in Example 4.

EXAMPLE 6

2N-Sodium hydroxide (50ml.) was added to a solution of ethyl 1-(7-chloroquinol-4-yl)-5-methoxy-2-methylindol-3-ylacetate (2g.) in ethanol (50ml.), and the mixture was heated at 80° C. for 15 minutes. The ethanol was evaporated in vacuo, and the residue was diluted with water (50ml.). The resulting mixture was filtered, and the solid residue was dissolved in water (30ml.). The solution was adjusted to pH 5 with concentrated hydrochloric acid, and the resulting precipitate was filtered off and dried at 60° C. There was thus obtained 1-(7-chloroquinol-4-yl)-5-methoxy-2-methylindol-3-ylacetic acid, m.p. 248°–250° C.

EXAMPLE 7

A mixture of ethyl 5-methoxy-2-methyl-1-quinol-4-ylindol-3-ylacetate (1.8g.), ethanol (25ml.) and 2N-potassium hydroxide (25ml.) was heated under reflux for 15 minutes. Most of the ethanol was then evaporated in vacuo, and the residue was diluted with water (100ml.). The resulting mixture was filtered and the filtrate acidified to pH 5 with 2N-hydrochloric acid. The resulting mixture was filtered, and the solid residue was washed with water (2 × 20ml.) and dried at 60° C. There was thus obtained 5-methoxy-2-methyl-1-quinol-4-ylindol-3-ylacetic acid, m.p. 262°–265° C.

Similarly, from ethyl 5-methoxy-2-methyl-1-quinol-2-ylindol-3-ylacetate there was obtained 5-methoxy-2-methyl-1-quinol-2-ylindol-3-ylacetic acid, m.p. 173°–175° C., and from ethyl 5-methoxy-2-methyl-1-quinazolin-4-ylindol-3-ylacetate there was obtained 5-methoxy-2-methyl-1-quinazolin-4-ylindol-3-ylacetic acid monohydrate, m.p. 101°–103° C.

EXAMPLE 8

The method described in Example 4 was carried out using ethyl 5-methoxy-2-methyl-1-(2-phenylquinol-4-yl)indolin-3-ylacetate as starting material. There was thus obtained ethyl 5-methoxy-2-methyl-1-(2-phenylquinol-4-yl)indol-3-ylacetate, NMR: $-OCH_3$ τ6.12. The product was shown to be pure by TLC on silica gel; elution with 5:1 ether: petroleum ether (b.p. 40°–60° C.).

The indoline derivative used as starting material was obtained by the method described above in respect of compounds of the formula XII, and it had NMR: $-OCH_3$ τ6.15. It was shown to be pure by TLC on silica gel; elution with 1:1 ether: petroleum ether (b.p. 40°–60° C.).

EXAMPLE 9

In a similar manner to that described in Example 5, starting with methyl 1-(7-chloroquinol-4-yl)-2-methylindolin-3-ylacetate, there was obtained methyl 1-(7-chloroquinol-4-yl)-2-methylindol-3-ylacetate as an oil, NMR: $-OCH_3$ τ6.21.

In a similar manner, using 2,3-dichloro-5,6-dicyano-1,4-benzoquinone instead of 2,3,5,6-tetrachloro-1,4-benzoquinone, from ethyl 1-(6-chloro-4-methylquinol-2-yl)-5-methoxy-2-methylindolin-3-ylacetate, there was obtained ethyl 1-(6-chloro-4-methylquinol-2-yl)-5-methoxy-2-methylindol-3-ylacetate, m.p. 137°–138° C., and from ethyl 1-(7-chloro-2-methylquinol-4-yl)-5-methoxy-2-methylindolin-3-ylacetate there was obtained ethyl 1-(7-chloro-2-methylquinol-4-yl)-5-methoxy-2-methylindol-3-ylacetate as an oil, NMR: $-OCH_3$ τ6.17.

The following indoline derivatives used as starting materials were prepared in a similar manner to that described in Example 4 for the preparation of ethyl 5-methoxy-2-methyl-1-(4-methyl-2-phenylpyrimidin-6-yl)indolin-3-ylacetate:

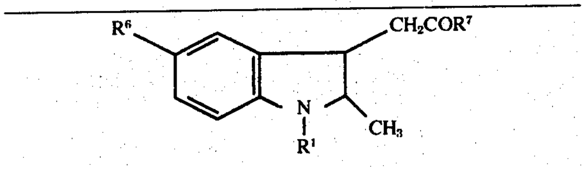

| $R^1$ | $R^7$ | $R^6$ | Characteristic properties |
|---|---|---|---|
| 7-chloroquinol-4-yl | $-OCH_3$ | H | NMR $-OCH_3$ τ6.22 Shown to be pure by TLC* |
| 6-chloro-4-methylquinol-2-yl | $-OCH_2CH_3$ | $OCH_3$ | NMR $-OCH_3$ τ6.15 Shown to be pure by TLC* |
| 7-chloro-2-methylquinol-4-yl | $-OCH_2CH_3$ | $OCH_3$ | NMR $-OCH_3$ τ6.18 Shown to be pure by TLC* |

*System A.

EXAMPLE 10

In analogous manner to that described in Example 7, the following compounds were prepared from the appropriate methyl or ethyl ester:

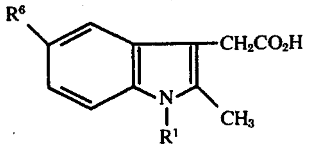

| $R^1$ | $R^6$ | Characteristic properties |
|---|---|---|
| 7-chloroquinazolin-4-yl | methoxy | m.p.94–95° C. (hemihydrate) |
| 6-chloro-4-methyl-quinol-2-yl | methoxy | m.p.226–227° C. (monohydrate) |
| 7-chloro-2-methyl-quinol-4-yl | methoxy | m.p.258–259° C. |
| 7-chloroquinol-4-yl | H | m.p.113–115° C.(hemihydrate) |
| 7-chlorocinnolin-4-yl | methoxy | m.p.190–193° C.(dec.) |
| quinazolin-4-yl | H | m.p.240–241° C.(dec.) |

EXAMPLE 11

A solution of methyl 1-(7-chlorocinnolin-4-yl)-5-methoxy-2-methylindolin-3-ylacetate (7.9g.) in dry 1,2-dimethoxyethane [80ml.; dried over sodium alumino-silicate (molecular sieve type 4A; obtainable from BDH Chemicals Ltd., Poole, England)] was mixed with a solution of 2,3-dichloro-5,6-dicyano-1,4-benzoquinone (4.5g.) in dry 1,2-dimethoxyethane (30ml.). The solution was heated under reflux for 20 minutes and then evaporated in vacuo. The residue was extracted with chloroform (5 × 50ml.). Evaporation of the extracts gave an oil, which was purified by chromatography on silica gel (350g.), using ether as eluant, to give methyl 1-(7-chlorocinnolin-4-yl)-5-methoxy-2-methylindol-3-ylacetate as a red syrup, homogeneous by thin layer chromatography (ether: silica gel) [hereinafter referred to as system C], and having a satisfactory NMR spectrum (5-$OCH_3$, τ6.13).

In a similar manner there were obtained from the appropriate indoline derivatives: methyl 1-(7-chloroquinazolin-4-yl)-5-methoxy-2-methylindol-3-ylacetate (m.p. 112°–114° C.), methyl 1-(6,8-dichloroquinazolin-4-yl)-5-methoxy-2-methylindol-3-ylacetate (m.p. 135°–137° C.), and methyl 2-methyl-1-quinazolin-4-ylindol-3-ylacetate [syrup, pure by TLC (systems A and C) and NMR spectroscopy ($-OCH_3$, τ6.1)].

The indoline derivatives used as starting materials were prepared in a similar manner to ethyl 1-quinazolin-4-yl-indolin-3-ylacetate, as described in Example 4:

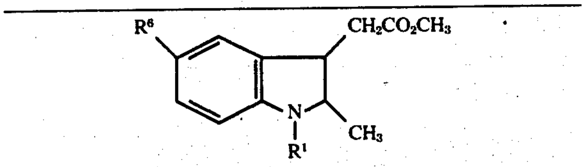

| $R^6$ | $R^1$ | Characteristic properties |
|---|---|---|
| $CH_3O$ | 7-chlorocinnolin-4-yl | orange syrup; NMR: $-OCH_3$ at 6.15τ; shown to be pure by TLC (System C) |
| $CH_3O$ | 7-chloroquinazolin-4-yl | yellow syrup: NMR: $-OCH_3$ |

-continued

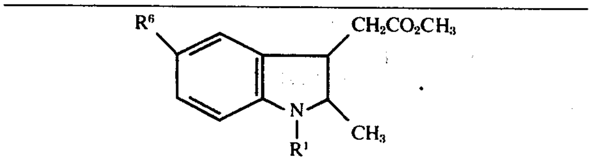

| $R^6$ | $R^1$ | Characteristic properties |
|---|---|---|
| | | at 6.13τ; shown to be pure by TLC (System A) |
| H | quinazolin-4-yl | yellow solid; m.p.109–110° C.; pure by TLC (Systems A and C) |
| $CH_3O$ | 6,8-dichloroquinazolin-4-yl | yellow syrup; pure by TLC (Systems A and C) |

EXAMPLE 12

5-Methoxy-2-methyl-1-quinol-4-ylindol-3-ylacetic acid (2g.) in methanol (30ml.) containing concentrated sulphuric acid (1 ml.) was refluxed for 2 hours. The resulting red solution was treated with saturated methanolic sodium acetate solution (30ml.) and the methanol then evaporated in vacuo. The residue was diluted with water (50ml.) and extracted with diethyl ether (2 × 30ml.). The ether extracts were dried ($MgSO_4$) and evaporated, to yield methyl 5-methoxy-2-methyl-1-quinol-4-ylindol-3-ylacetate, m.p. 103°–105° C.

EXAMPLE 13

Ethyl 5-methoxy-2-methyl-1-(2-phenylquinol-4-yl)indol-3-ylacetate (2.1g.) in ethanol (20ml.) and 2N-sodium hydroxide solution (20ml.) was refluxed for 0.25 hour. Most of the ethanol was removed in vacuo and the residue was diluted with water (50ml.). The resulting mixture was filtered, and the residue was washed with water and dried at 60° C. to give 5-methoxy-2-methyl-1-(2-phenylquinol-4-yl)indol-3-ylacetic acid sodium salt monohydrate, m.p. 179°–180° C.

EXAMPLE 14

A mixture of 1-(7-chloroquinol-4-yl)-5-methoxy-2-methylindolin-3-ylacetic acid (1g.) and 2,3,5,6-tetrachloro-1,4-benzoquinone (1g.) in dry xylene (50ml.) was refluxed for 2 hours. The solvent was removed in vacuo and the residue adsorbed on a column of chromatographic silica gel (50g.). The column was eluted with chloroform containing increasing amounts of methanol (starting with pure chloroform, and then using increments of 1% v/v of methanol in chloroform; product mainly eluted with 5% methanol in chloroform) to give 1-(7-chloroquinol-4-yl)-5-methoxy-2-methylindol-3-ylacetic acid, m.p. 248°–250° C.

the indoline derivative used as starting material was prepared from ethyl 1-(7-chloroquinol-4-yl)-5-methoxy-2-methylindolin-3-ylacetate in a similar manner to that described in Example 7; it had m.p. 248°–250° C.

EXAMPLE 15

A solution of methyl 1-(7-chloroquinazolin-4-yl)-5-methoxy-2-methylindolin-3-ylacetate hydrochloride (2.15g.) in dry dimethylformamide (50ml.; dried with calcium hydride) was treated with 2,3-dichloro-5,6-dicyano-1,4-benzoquinone (1.2g.). The mixture was heated on a steam bath for 2 hours and then an additional portion of the benzoquinone derivative (0.6g.) was added. After further heating for 1 hour, the solution was poured into water (500ml.) containing anhydrous sodium acetate (10g.). The mixture was extracted with chloroform (3 × 100ml.) and the solid residue, at the solvent interface, discarded. The chloroform extracts were washed successively with water, saturated sodium bicarbonate solution, water and brine, and then dried ($MgSO_4$). Evaporation of the solution gave an oil, which was purified by chromatography on silica gel (100g.) in an increasing gradient of ether in petroleum ether (b.p. 40°–60° C.) (polarity increased by incremental addition of 10% v/v ether) to give methyl 1-(7-chloroquinazolin-4-yl)-5-methoxy-2-methylindol-3-ylacetate as a yellow solid, m.p. 112°–114° C.

The starting material was prepared as follows:

A mixture of methyl 5-methoxy-2-methylindolin-3-ylacetate (9.5g.) and 4,7-dichloroquinazoline (8.0g.) in dry 1,2-dimethoxyethane (100ml.; dried over sodium alumino-silicate, see Example 11) was heated under reflux for 1 hour. The mixture was cooled to 20°–25° C. and the resulting mixture filtered to give methyl 1-(7-chloroquinazolin-4-yl)-5-methoxy-2-methylindolin-3-yl)acetate hydrochloride, m.p. 188°–190° C. (decomposition).

EXAMPLE 16

A stirred suspension of sodium hydride (0.24g.) in dry dimethylformamide (20ml.; dried with calcium hydride) was treated at 5°–10° C. with a solution of ethyl 2-methyl-5-methoxyindol-3-ylacetate (2.3g.) in dry dimethylformamide (10ml.). The mixture was stirred at 25°–30° C. for 15 minutes, and the solution obtained was treated with a freshly prepared solution of 4-chloroquinazoline (1.65g.) in dry dimethylformamide (10ml.). The mixture was stirred at 30°–40° C, for 4 hours, and then poured into water (500ml.). The mixture was extracted with ethyl acetate (4 × 100ml.) and the extracts washed successively with water (2 × 100ml.) and brine (100ml.), and then dried (sodium sulphate). Evaporation of solvent gave an oil which was purified by chromatography on silica gel (250g.) using an increasing gradient of ether in petroleum ether (b.p. 40°–60° C.) (the polarity increased by incremental addition of 10% v/v ether) to give ethyl 5-methoxy-2-methyl-1-(quinazolin-4-yl)indol-3-ylacetate, m.p. 121°–123° C.

In a similar manner there was obtained methyl 1-(7-chloroquinazolin-4-yl)-5-methoxy-2-methylindol-3-ylacetate, m.p. 112°–114° C., from the appropriate starting materials.

EXAMPLE 17

A solution of ethyl laevulinate p-methoxyphenylhydrazone (2.64g.) in dry 1,2-dimethoxyethane (30ml.; dried over sodium alumino-silicate, see Example 11) was treated with a solution of 4-chloroquinazoline (1.7g.) in dry 1,2-dimethoxyethane (20ml.). The resulting solution was heated under reflux for 4 hours and then concentrated in vacuo. To the residue was added a saturated solution of sodium acetate (30ml.), and the mixture was extracted with ethyl acetate (50ml.). The aqueous phase was separated and further extracted with ethyl acetate (3 × 50ml.). The combined ethyl acetate extracts were washed successively with water (50ml.), saturated sodium bicarbonate solution (50ml.), water (50ml.) and brine (50ml.), and then dried (magnesium sulphate) and evaporated in vacuo. The residual syrup was chromatographed on silica (300g.) using an increasing gradient of ether in petroleum ether (b.p. 40°–60° C.) (polarity increased by incremental addition of 10% v/v ether) to give ethyl 5-methoxy-2-methyl-1-(quinazolin-4-yl)indol-3-ylacetate, m.p. 121°–123° C.

In a similar manner there was obtained methyl 2-methyl-5-methoxy-1-(7-chloroquinazolin-4-yl)indol-3-ylacetate, m.p. 112°–114° C., from the appropriate starting materials.

EXAMPLE 18

A mixture of laevulinic acid (15g.) and acetaldehyde $N^1$-(7-chloroquinazolin-4-yl)-p-methoxyphenylhydrazone hydrochloride (3.3g.) was heated at 95°–100° C. for 18 hours. The mixture was poured into water (ca 300ml.), and the precipitated pale yellow solid was collected by filtration and dissolved in a mixture of water (80ml.) and ammonia solution (specific gravity 0.88, ca 5ml.). The solution was washed with ethyl acetate (2 × 25ml.). Addition of sodium chloride (ca 10g.) to the aqueous phase caused a yellow solid to precipitate. This was collected by filtration, and then dissolved in water. The solution was acidified with glacial acetic acid until precipitation was complete. The mixture was filtered to give, as solid residue, 2-methyl-5-methoxy-1-(7-chloroquinazolin-4-yl)indol-3-ylacetic acid monohydrate, m.p. 98°–100° C.

The starting material was obtained as follows:

To a solution of 4,7-dichloroquinazoline (2.0g.) in dry 1,2-dimethoxyethane (50ml.; dried over sodium aluminosilicate, see Example 11) was added acetaldehyde p-methoxyphenylhydrazone (1.6g.), and the mixture was heated under reflux for 30 minutes. The mixture was cooled to ca 25° C. and the precipitate of acetaldehyde $N^1$-(7-chloroquinazolin-4-yl)-p-methoxyphenylhydrazone hydrochloride, m.p. 193°–195° C. (decomposition), was collected by filtration.

EXAMPLE 19

In an analogous manner to that described in Example 4, the following compounds were prepared:

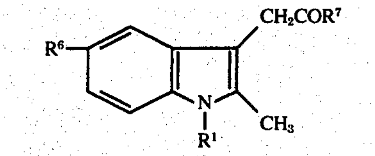

| Compound number (see below) | $R^1$ | $R^7$ | $R^6$ | Characteristic Properties |
|---|---|---|---|---|
| (1) | quinazolin-4-yl | methoxy | dimethyl-amino | m.p. 142–145° C. |
| (2) | 6-methoxy-4-methyl-quinol-2-yl | ethoxy | methoxy | NMR:—$OCH_3$ at 6.1τ; pure by TLC (on silica gel: elution with ether: petroleum ether (b.p.40–60° C.)1:3)* |
| (3) | 7-methylquinol-4-yl | methoxy | methoxy | NMR:5—$OCH_3$ at 6.1τ; pure by TLC (System C) |
| (4) | quinoxalin-2-yl | methoxy | methoxy | m.p. 110–112° C. |

*TLC system hereinafter referred to as system D

The indoline derivative used as starting material in the preparation of compound (1) above, i.e. methyl 5-dimethylamino-2-methyl-1-quinazolin-4-ylindolin-3-ylacetate, was prepared as follows:

A solution of methyl 1-acetyl-2-methylindolin-3-ylacetate (6.83 g.) in concentrated sulphuric acid (45 ml.) was cooled to 0° C. and a solution of sodium nitrate (2.67 g.) in concentrated sulphuric acid (20 ml.) was added dropwise during 0.5 hr. The mixture was stirred at 0° C. for a further 0.5 hr. and then poured onto ice (300 ml.). The resulting precipitate was filtered and washed well with water. Crystallisation from methanol gave methyl 1-acetyl-2-methyl-5-nitroindolin-3-ylacetate, m.p. 106° C.

A solution of this nitro derivative (12.3 g.) in methanol (400 ml.) containing 37% w/v formalin solution (7 ml.) was shaken with 10% w/w palladium on charcoal (10.5 g) in an atmosphere of hydrogen at room temperature and atmospheric pressure. The hydrogen uptake was 5150 ml. After hydrogenation, the catalyst was filtered off and the filtrate evaporated in vacuo. The residue was crystallised from benzene to give methyl 1-acetyl-5-dimethylamino-2-methylindolin-3-ylacetate, m.p. 122° C.

A solution of this dimethylamino derivative (8 g.) in methanol (125 ml.) was refluxed for 1 hour whilst a stream of hydrogen chloride gas was passed through it. Anhydrous sodium acetate (5 g.) was added to the reaction mixture, and the bulk of the methanol removed in vacuo at 40° C.

The residue was dissolved in ether (50 ml.), and the solution was washed successively with saturated aqueous sodium acetate solution (20 ml.) and water (20 ml.). The ethereal solution was dried ($MgSO_4$) and evaporated to yield methyl 5-dimethylamino-2-methylindolin-3-ylacetate as an oil, shown to be pure by TLC (System C).

This indoline derivative was then reacted with 4-chloroquinazoline in a similar manner to that described in Example 4 for the preparation of ethyl 1-quinazolin-4-ylindolin-3-ylacetate, and there was obtained methyl 5-dimethylamino-2-methyl-1-quinazolin-4-ylindolin-3-ylacetate, as a syrup which was shown to be pure by TLC (systems A and B).

The indoline derivatives used as starting materials in the preparation of compounds (2) and (3) in the above table were prepared in a similar manner to that described in Example 4 for ethyl 5-methoxy-2-methyl-1-(4-methyl-2-phenylpyrimidin-6-yl)indolin-3-ylacetate. Both compounds had NMR. $-OCH_3$ at 6.2 τ, and both were shown to be pure by TLC (systems A, C and D)

The indoline derivative used as starting material in the preparation of compound (4) in the above table was prepared as follows:

Anhydrous sodium acetate (3.6 g.) was added to a mixture of methyl 5-methoxy-2-methylindolin-3-ylacetate (8.0 g.) and 2,3-dichloroquinoxaline (6.8 g.) in diethyleneglycol dimethyl ether (150 ml.), and the mixture was heated under reflux for 12 hrs. The mixture was then cooled and poured into water (800 ml.), and the aqueous suspension was extracted with ethyl acetate (3 × 50 ml.). The combined extracts were washed successively with water (4 × 30 ml.) and a saturated aqueous solution of sodium chloride (50 ml.), and then dried ($MgSO_4$) and evaporated. The resultant syrup was chromatographed on chromatographic silica gel (M.F.C., 300 g.) using an increasing gradient of diethyl ether in petroleum ether (b.p. 40°–60° C.) (polarity increased by incremental addition of 10% v/v ether.) The combined eluate was evaporated to give methyl 1-(3-chloroquinoxalin-2-yl)-5-methoxy-2-methylindolin-3-ylacetate, m.p. 155°–157° C.

EXAMPLE 20

In analogous manner to that described in Example 7, the following compounds were prepared from the appropriate methyl or ethyl ester:

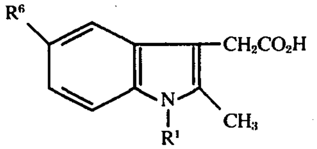

| $R^1$ | $R^6$ | Characteristic properties |
|---|---|---|
| 6-chloroquinol-2-yl | methoxy | m.p. 193–195° C. |
| 8-chloroquinol-4-yl | methoxy | m.p. 272–273° C. (hemihydrate) |
| 7-bromoquinol-4-yl | methoxy | m.p. 251–253° C. (hemihydrate) |
| 7-methoxyquinol-4-yl | methoxy | m.p. 123–125° C. (hemihydrate) |
| 7-methylquinol-4-yl | methoxy | m.p. 268–269° C. |
| 6-methoxy-4-methylquinol-2-yl | methoxy | m.p. 108–110° C. (hemihydrate) |
| isoquinol-1-yl | methoxy | m.p. 195° C. (hemihydrate) |
| 7-chloroquinazolin-4-yl | methyl | m.p. 115–118° C. |
| 7-trifluoromethylquinol-4-yl | methoxy | m.p. 180–182° C. |
| 6,7-dichloroquinol-4-yl | methoxy | m.p. 258–260° C. |
| 6-chloro-4-phenylquinazolin-2-yl | methoxy | m.p. 98–100° C. (monohydrate) |

EXAMPLE 21

In analogous manner to that described in Example 11 the following compounds were prepared from the appropriate starting materials using either 2,3-dichloro-5,6-dicyano-1, 4-benzoquinone (DDQ) or 2,3,5,6-tetrachloro-1,4-benzoquinone(CA):

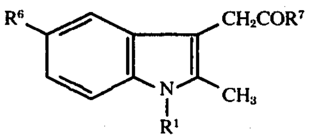

| $R^1$ | $R^7$ | $R^6$ | Characteristic properties | Quinone used |
|---|---|---|---|---|
| 7-chloroquinazolin-4-yl | methoxy | methyl | NMR: $-CH_3$ at 7.6τ; pure by TLC (System A). | DDQ |
| 6-chloroquinol-2-yl | methoxy | methoxy | m.p. 104–105° C. | DDQ |
| 8-chloroquinol-4-yl | methoxy | methoxy | NMR:5-$OCH_3$ at 6.18τ; pure by TLC (System C) | DDQ |
| 7-bromoquinol-4-yl | methoxy | methoxy | NMR:5-$OCH_3$ at 6.20τ; pure by TLC (System C) | DDQ |
| 6-chloro-4-phenyl-quinazolin-2-yl | ethoxy | methoxy | m.p. 143–144° C. | DDQ |
| 6,7-dichloroquinol-4-yl | methoxy | methoxy | NMR:5-$OCH_3$ at 6.15τ; pure by TLC (Systems A and C) | DDQ |
| 7-trifluoromethyl-quinol-4-yl | methoxy | methoxy | NMR:5-$OCH_3$ at 6.20τ; pure by TLC (Systems A and C) | DDQ |
| 7-methoxyquinol-4-yl | methoxy | methoxy | NMR:5-$OCH_3$ at 6.18τ; pure by TLC (System C) | CA |
| isoquinol-1-yl | methoxy | methoxy | NMR:5-$OCH_3$ at 6.22τ; pure by TLC (Systems A and C) | CA |

The starting material used in the preparation of the first compound in the above table, i.e. methyl 1-(7-chloroquinazolin-4-yl)-2,5-dimethylindolin-3-ylacetate, was obtained in an analogous manner to that described in Example 4 for the preparation of ethyl 1-quinazolin-4-ylindolin-3-ylacetate. The compound had NMR: $—CH_3$ at 7.6 $\tau$ and was shown to be pure by TLC (Systems A and B).

The indoline derivatives used as starting materials in the preparation of all of the other compounds in the above table were prepared in analogous manner to that described in Example 4 for the preparation of ethyl 5-methoxy-2-methyl-1-(4-methyl-2-phenylpyrimidin-6-yl)indolin-3-ylacetate, and they have the following characteristic properties:

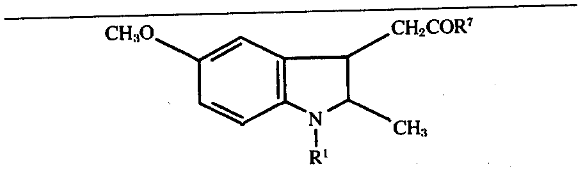

| $R^1$ | $R^7$ | Characteristic properties |
|---|---|---|
| 6-chloroquinol-2-yl | methoxy | m.p. 128–130° C. |
| 8-chloroquinol-4-yl | methoxy | NMR:5-$OCH_3$ at 6.20$\tau$; pure by TLC (System C) |
| 7-bromoquinol-4-yl | methoxy | NMR:5-$OCH_3$ at 6.18$\tau$; pure by TLC (System C) |
| 6-chloro-4-phenyl-quinazolin-2-yl | ethoxy | m.p. 174–175° C. |
| 6,7-dichloroquinol-4-yl | methoxy | NMR:5-$OCH_3$ at 6.15$\tau$; pure by TLC (Systems A and C) |
| 7-trifluoromethyl-quinol-4-yl | methoxy | NMR:5-$OCH_3$ at 6.20$\tau$; pure by TLC (Systems A and C) |

–Continued

| $R^1$ | $R^7$ | Characteristic properties |
|---|---|---|
| 7-methoxyquinol-4-yl | methoxy | NMR:5-$OCH_3$ at 6.17$\tau$; pure by TLC (System C) |
| isoquinol-1-yl | methoxy | NMR:5-$OCH_3$ at 6.20$\tau$; pure by TLC (System A and C) |

EXAMPLE 22

In a similar manner to that described in Example 17, but starting with ethyl $\alpha$-methyllaevulinate p-methoxyphenylhydrazone, there was obtained ethyl $\alpha$-[1-(7-chloroquinazolin-4-yl)-5-methoxy-2-methylindol-3-yl]propionate as a viscous syrup which was pure by TLC (System C) and had NMR: $—OCH_3$ at 6.20 $\tau$.

EXAMPLE 23

In a similar manner to that described in Example 18, (but the ammonium salt was not isolated in every case) the following compounds were obtained from the appropriate phenylhydrazone derivatives:

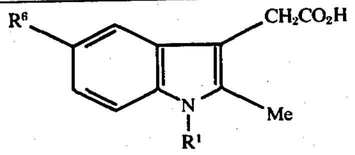

| $R^1$ | $R^6$ | Characteristic properties |
|---|---|---|
| 7-fluoroquinazolin-4-yl | methoxy | m.p. 90–93° C.(hemihydrate) |
| 7-bromoquinazolin-4-yl | methoxy | m.p. 104–106° C.(hemihydrate) |
| 8-chloroquinazolin-4-yl | methoxy | m.p. 102–105° C.(hemihydrate) |
| 7-methylquinazolin-4-yl | methoxy | m.p. 95–100° C.(monohydrate) |
| 7-chloroquinazolin-4-yl | methyl | m.p. 115–118° C. |
| 2-methylquinazolin-4-yl | methoxy | m.p. 97–99° C.(hemihydrate) |

In a similar manner, using $\alpha$-methyllaevulinic acid and acetaldehyde $N^1$-(7-chloroquinazolin-4-yl)-p-methoxyphenylhydrazone hydrochloride as starting materials, there was obtained $\alpha$-[1-(7-chloroquniazolin-4-yl)-5-methoxy-2-methylindo-3-yl]propionic acid, m.p. 110°–112° C.

The following hydrazone derivatives, used as starting materials in preparing the indole derivatives described in this Example (except for the last, in respect of which see Example 18), were prepared in a similar manner to that described in Example 18:

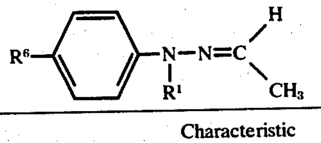

| $R^1$ | $R^6$ | Characteristic properties |
|---|---|---|
| 7-fluoroquinazolin-4-yl | methoxy | NMR: $—OCH_3$ at 6.13$\tau$; pure by TLC (Systems A and D) |
| 7-bromoquinazolin-4-yl | methoxy | m.p. 156–158° C. |
| 8-chloroquinazolin-4-yl | methoxy | NMR: $—OCH_3$ at 6.20$\tau$; pure by TLC (Systems A and C) |
| 7-methylquinazolin-4-y- | methoxy | m.p. 130–132° C. |
| 7-chloroquinazolin-4-yl | methyl | m.p. 200–205° C. (decomposition) (hydrochloride) |
| 2-methylquinazolin-4-yl | methoxy | m.p. 190–192° C. (hydrochloride) |

EXAMPLE 24

Methyl 1-(7-chloroquinol-4-yl)-5-methoxy-2-methylindol-3-ylacetate (1.7g.) in methanol (50ml.) containing 30% w/v methylamine solution (25ml.) was refluxed for 10 hours. The solvents were evaporated in vacuo and the residue crystallised from a 1:1 v/v mixture of benzene and cyclohexane to give 1-(7-chloroquinol-4-yl)-5-methoxy-N,2-dimethylindol-3-ylacetamide, m.p. 168°–169° C.

In a similar manner, from methyl 1-(7-chloroquinol-4-yl)-5-methoxy-2-methylindol-3-ylacetate and ammonium hydroxide solution (specific gravity 0.88) there was obtained 1-(7-chloroquinol-4-yl)-5-methoxy-2-methylindol-3-ylacetamide, m.p. 147°–148° C., and from methyl 1-(7-chloroquinol-4-yl)-5-methoxy-2-methylindol-3-ylacetate and hydrazine hydrate solution there was obtained 1-(7-chloroquinol-4-yl)-5-methoxy-2-methylindol-3-yl-acetohydrazide, m.p. 183°–184° C., and from methyl 1-(7-chloroquinazolin-4-yl)-5-methoxy-2-methylindol-3-ylacetate and hydrazine hydrate solution, there was obtained 1-(7-chloroquinazolin-4-yl)-5-methoxy-2-methylindol-3-ylacetohydrazide, m.p. 164°–165° C.

EXAMPLE 25

A solution of anhydrous 1-(7-chloroquinazolin-4-yl)-5-methoxy-2-methylindol-3-ylacetic acid (1.9g.) in ethanol-free chloroform (30ml., dried with calcium chloride) was treated with triethylamine (0.5ml.; dried over potassium hydroxide pellets) at 0° C. A solution of ethyl chloroformate (0.48ml.) in dry, ethanol-free, chlorofrom (10ml.) was then added, and the mixture stirred at 0° C. for 1½ hours. A solution of 2-N,N-dimethylaminoethanol (0.56ml.) in chloroform (5ml.) was then added. The mixture was heated under reflux for 2 hours, and then added to water (100ml.). The chloroform layer was separated, washed with water, dried ($MgSO_4$), and evaporated. The residual oil was purified by chromatography on silica gel (150g.) in a mixture of 5% v/v methanol and 95% v/v chloroform to give, after the elution of low polarity impurities, β-(N,N-dimethylamino)ethyl 1-(7-chloroquinazolin-4-yl)-5-methoxy-2-methylindol-3-ylacetate as a pale yellow oil, NMR: $OCH_3$ at 6.23τ.

In a similar manner, starting with the appropriate 1-substituted indol-3-ylacetic acid and the appropriate alcohol or phenol, there were obtained:

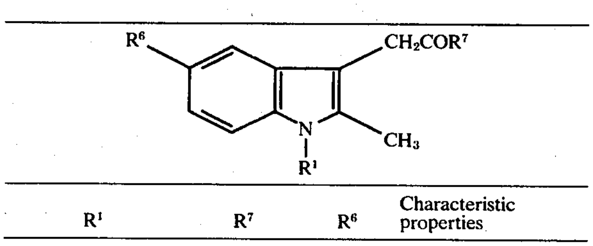

| $R^1$ | $R^7$ | $R^6$ | Characteristic properties |
|---|---|---|---|
| 7-chloroquinazolin-4-yl | n-butoxy | methoxy | syrup; NMR:5-$OCH_3$, 6.2τ; pure by TLC (Systems A and C) |
| 7-chloroquinazolin-4-yl | ethoxy | methoxy | m.p.103–105° C. |
| 7-chloroquinazolin-4-yl | benzyloxy | methoxy | syrup; NMR:5-$OCH_3$, 6.23τ; pure by TLC (Systems A and D) |

–Continued

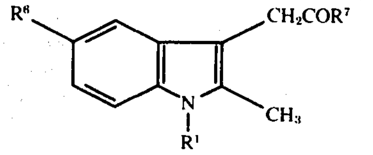

| $R^1$ | $R^7$ | $R^6$ | Characteristic properties |
|---|---|---|---|
| 7-chloroquinazolin-4-yl | phenoxy | methoxy | syrup; NMR:5-$OCH_3$, 6.15τ; pure by TLC (Systems A and D) |
| 7-chloroquinazolin-4-yl | cyclohexylmethoxy | methoxy | syrup; NMR:5-$OCH_3$, 6.2τ; pure by TLC (Systems A and D) |
| 7-chloroquinazolin-4-yl | phenoxy | methyl | syrup; NMR:5-$CH_3$, 7.55τ; pure by TLC (Systems A and D) |
| 7-chloroquinazolin-4-yl | phenoxy | fluoro | m.p.122–124° C. |
| 7-chloroquinazolin-4-yl | ethoxy | fluoro | syrup; NMR:2-$CH_3$, 7.7τ; pure by TLC (Systems A and D) |
| 7-chloroquinazolin-4-yl | methoxy | methyl | syrup; NMR:5-$CH_3$, 7.6τ; pure by TLC (Systems A and C) |
| 7-chlorocinnolin-4-yl | methoxy | methoxy | syrup; NMR:5-$OCH_3$, 6.13τ; pure by TLC (System C) |
| quinazolin-4-yl | ethoxy | methoxy | m.p.121–123° C. |
| 7-chloroquinazolin-4-yl | methoxy | methoxy | m.p.112–114° C. |
| 7-chloroquinol-4-yl | methoxy | methoxy | m.p.103–105° C. |

EXAMPLE 26

In a similar manner to that described in Example 25, but starting with the appropriate 1-substituted-indol-3-ylacetic acid and amine, there were obtained the following amides:

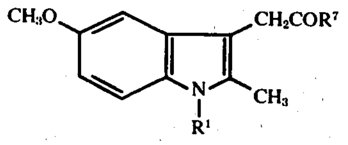

| $R^1$ | $R^7$ | Characteristic properties |
|---|---|---|
| 7-chloroquinol-4-yl | NHMe | m.p.168–169° C. |
| 7-chloroquinol-4-yl | $NH_2$ | m.p.147–148° C. |
| 7-chloroquinol-4-yl | $NHNH_2$ | m.p.183–184° C. |
| 7-chloroquinazolin-4-yl | NHPh | m.p.132–133° C. |
| 7-chloroquinazolin-4-yl | $NH_2$ | m.p.197–198° C. |
| 7-chloroquinazolin-4-yl | $NHNH_2$ | m.p.164–165° C. |

EXAMPLE 27

A mixture of phenol (0.27g.) and anhydrous 1-(7-chloroquinazolin-4-yl)-5-methoxy-2-methylindol-3-ylacetic acid (1.0g.) in dry 1,2-dimethoxyethane (20ml.; dried over sodium aluminosilicate powder) was stirred at room temperature and treated with dicyclohexylcarbodiimide (0.75g.). The mixture became opaque, and was stirred overnight at room temperature and then filtered. Evaporation of the filtrate gave a dark yellow syrup, which was purified by chromatography on silica gel (175g.), using an increasing gradient of ether in petroleum ether (b.p. 40°–60° C.) (polarity increased by incremental addition of 10% v/v ether).

The major product, phenyl 1-(7-chloroquinazolin-4-yl)-5-methoxy-2-methylindol-3-ylacetate, was obtained as a yellow glass (NMR: $OCH_3$ at 6.20τ; pure by TLC: systems A and D), from the petrol rich fractions. A second product, 1-[1-(7-chloroquinazolin-4-yl)-5-methoxy-2-methylindol-3-ylacetyl]-1,3-dicyclohexylurea, was obtained as a pale yellow solid of m.p. 105°–107° C. NMR: $OCH_3$ at 6.23τ; pure by TLC: system C).

In a similar manner, starting with the appropriate 1-substituted indol-3-ylacetic acid and the alcohol or phenol, there were obtained:

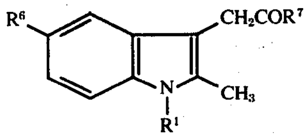

| $R^1$ | $R^7$ | $R^6$ | Characteristic properties |
|---|---|---|---|
| 7-chloroquinazolin-4-yl | n-butoxy | methoxy | syrup; NMR:5-$OCH_3$, 6.2τ; pure by TLC (Systems A and C) |
| 7-chloroquinazolin-4-yl | ethoxy | methoxy | m.p.103–105° C. |
| 7-chloroquinazolin-4-yl | benzyloxy | methoxy | syrup; NMR:5-$OCH_3$, 6.23τ; pure by TLC (Systems A and D) |
| 7-chloroquinazolin-4-yl | cyclo-hexyl-methoxy | methoxy | syrup; NMR:5-$OCH_3$, 6.2τ; pure by TLC (Systems A and D) |
| 7-chloroquinazolin-4-yl | phenoxy | methyl | syrup; NMR:5-$CH_3$, 7.55τ; pure by TLC (Systems A and D) |
| 7-chloroquinazolin-4-yl | phenoxy | fluoro | m.p.122–124° C. |
| 7-chloroquinazolin-4-yl | ethoxy | fluoro | syrup; NMR:2-$CH_3$, 7.7τ; pure by TLC (Systems A and D) |
| 7-chloroquinazolin-4-yl | methoxy | methyl | syrup; NMR:5-$CH_3$, 7.6τ; pure by TLC (Systems A and C) |
| 7-chlorocinnolin-4-yl | methoxy | methoxy | syrup; NMR:5-$OCH_3$, 6.13τ; pure by TLC (System C) |
| quinazolin-4-yl | ethoxy | methoxy | m.p.121–123° C. |
| 7-chloroquinazolin-4-yl | methoxy | methoxy | m.p.112–114° C. |
| 7-chloroquinol-4-yl | methoxy | methoxy | m.p.103–105° C. |

EXAMPLE 28

In a similar manner to that described in Example 27 but starting with the appropriate 1-substituted-indol-3-ylacetic acid and amine, there were prepared the following amides:

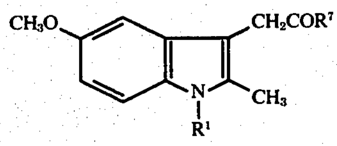

| $R^1$ | $R^7$ | Characteristic properties |
|---|---|---|
| 7-chloroquinol-4-yl | NHMe | m.p.168–169° C. |
| 7-chloroquinol-4-yl | $NH_2$ | m.p.147–148° C. |
| 7-chloroquinol-4-yl | $NHNH_2$ | m.p.183–184° C. |
| 7-chloroquinazolin-4-yl | NHPh | m.p.132–133° C. |
| 7-chloroquinazolin-4-yl | $NH_2$ | m.p.197–198° C. |
| 7-chloroquinazolin-4-yl | $NHNH_2$ | m.p.164–165° C. |

EXAMPLE 29

A solution of sodium (0.7g.) in dry methanol (30ml.; dried over sodium alumino-silicate) was added to a solution of 1-(2,6-dichloropyrimid-4-yl)-2,5-dimethylindol-3-ylacetic acid (3.5g.) in dry methanol (90ml.), and the mixture was heated under reflux for 2 hours. After removal of solvent under reduced pressure, the residue was dissolved in water (50ml.) and the solution acidified to pH 4 with acetic acid. The resulting mixture was filtered, and the solid residue crystallised from benzene to give 1-(2,6-dimethoxypyrimid-4-yl)-2,5-dimethylindol-3-ylacetic acid, m.p. 197°–198° C.

In a similar manner, starting with the appropriate 1-(2,6-dichloropyrimid-4-yl)indol-3-ylacetic acid, there were obtained 1-(2,6-dimethoxypyrimid-4-yl)-2-methylindol-3-ylacetic acid, m.p. 122°–123° C., and 1-(2,6-dimethoxypyrimid-4-yl)-5-methoxy-2-methylindol-3-ylacetic acid, m.p. 155°–158° C.

EXAMPLE 30

Methyl 1-(7-chloroquinol-4-yl)-5-methoxy-2-methylindol-3-ylacetate (1g.) and sodium borohydride (1g.) in methanol (30ml.) were refluxed for 1 hour. Most of the methanol was then removed in vacuo, and the residue was diluted with water (50ml.), and extracted with ethyl acetate (3 × 50ml.). The combined extracts were dried ($MgSO_4$) and evaporated to give an oil, which was chromatographed on silica gel (100g.) using, as eluant, petroleum ether (b.p. 40°–60° C.) containing an increasing proportion of ether (polarity increased by incremental addition of 10% v/v ether) to give 1-(7-chloroquinol-4-yl)-3-(2-hydroxyethyl)-5-methoxy-2-methylindole, m.p. 143°–145° C.

Similarly, from methyl 1-(7-chloroquinazolin-4-yl)-5-methoxy-2-methylindol-3-ylacetate, there was obtained 1-(7-chloroquinazolin-4-yl)-3-(2-hydroxyethyl)-5-methoxy-2-methylindole, m.p. 148°–150° C., and from methyl 1-(7-chloroquinazolin-4-yl)-2,5-dimethylindol-3-ylacetate, there was obtained 1-(7-chloroquinazolin-4-yl)-2,5-dimethyl-3-(2-hydroxyethyl)indole as a glass [pure by TLC (system A) and having a satisfactory NMR spectrum (—$CH_3$ at 7.6τ and —$CH_3$ at 7.7τ)].

EXAMPLE 31

A solution of 1-(7-chloroquinazolin-4-yl)-2,5-dimethylindol-3-ylacetic acid (1.8g.) in dimethylformamide (30ml.; dried by distillation from calcium hydride) was added to sodium hydride (0.13g.), and the mixture was stirred under a slight vacuum (ca 150mm. Hg) until complete dissolution occurred. Methyl iodide (2ml.) was then added, and the mixture was stirred for 2 hours at 40°–50° C. The mixture was then added to water (200ml.) and the resulting mixture extracted with ethyl acetate (3 × 50ml.). The combined extracts were washed successively with saturated sodium bicarbonate solution (3 × 30ml.), water and brine (50ml.). After drying ($MgSO_4$), the extracts were evaporated in vacuo to give methyl 1-(7-chloroquinazolin-4-yl)-2,5-dimethylindol-3-ylacetic acetate as a stiff syrup [NMR: 5—$CH_3$ at 7.6τ; pure by TLC (system A)].

In a similar manner, starting with the appropriate alkyl halide, there were obtained:

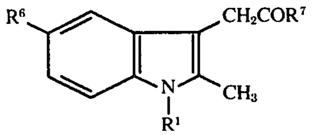

| $R^1$ | $R^7$ | $R^6$ | Characteristic properties |
|---|---|---|---|
| 7-chloroquinazolin-4-yl | n-butoxy | methoxy | syrup; NMR:5-$OCH_3$, 6.2τ; pure by TLC (Systems A and C) |
| 7-chloroquinazolin-4-yl | ethoxy | methoxy | m.p.103–105° C. |
| 7-chloroquinazolin-4-yl | benzyloxy | methoxy | syrup; NMR:5-$OCH_3$, 6.23τ; pure by TLC (Systems A and D) |
| 7-chloroquinazolin-4-yl | cyclohexyl-methoxy | methoxy | syrup; NMR:5-$OCH_3$, 6.2τ; pure by TLC (Systems A and D) |
| 7-chloroquinazolin-4-yl | ethoxy | fluoro | syrup; NMR:2-$CH_3$, pure by TLC (Systems A and D) |
| 7-chlorocinnolin-4-yl | methoxy | methoxy | syrup; NMR:5-$OCH_3$, 6.13τ; pure by TLC (System C) |
| quinazolin-4-yl | ethoxy | methoxy | m.p.121–123° C. |
| 7-chloroquinazolin-4-yl | methoxy | methoxy | m.p.112–114° C. |

EXAMPLE 32

A solution of acetaldehyde $N^1$-(7-chloroquinazolin-4-yl)p-methoxyphenylhydrazone hydrochloride (3.2g.) and 5-hydroxy-pentane-2-one (1.1g.) in ethanol (60ml.) was refluxed for 18 hours. The mixture was cooled and filtered and the filtrate evaporated in vacuo. The residue was chromatographed on silica gel (100g.) using, as eluant, petroleum ether (b.p. 40°–60° C.) containing an increasing proportion of ether (polarity increased by incremental addition of 10% v/v ether) to give 1-(7-chloroquinazolin-4-yl)-3-(2-hydroxyethyl)-5-methoxy-2-methylindole, m.p. 148°–150° C.

Similarly, from acetaldehyde $N^1$-(7-chloroquinazolin-4-yl)-p-methylphenylhydrazine hydrochloride and 5-hydroxypentan-2-one, there was obtained 1-(7-chloroquinazolin-4-yl)-2,5-dimethyl-3-(2-hydroxyethyl)indole as a glass [pure by TLC (system C) and having a satisfactory NMR spectrum (—$CH_3$ τ 7.60 and —$CH_3$ τ 7.70)].

EXAMPLE 33

A solution of 1-(7-chloroquinazolin-4-yl)-3-(2-hydroxyethyl)-5-methoxy-2-methylindole (0.6g.) and acetic anhydride (0.4g.) in benzene (20ml.; dried over sodium wire) was refluxed for 15 hours. The resulting yellow solution was cooled and washed successively with saturated sodium hydrogen carbonate solution (2 × 20ml.) and water (20ml.), and dried ($MgSO_4$). The solution was evaporated to give 2-[1-(7-chloroquinazolin-4-yl)-5-methoxy-2-methylindol-3-yl]ethyl acetate as an oil [pure by TLC (system A) and having a satisfactory NMR spectrum (—$OCH_3$ τ 6.18)].

EXAMPLE 34

A solution of ethyl 1-(7-chloroquinazolin-4-yl)-5-hydroxy-2-methylindol-3-ylacetate (1.0g.) in dry dimethyl-formamide (10ml.; dried by distillation from calcium hydride, and stored over sodium alumino-silicate) was added to sodium hydride (0.068g.), and the mixture was stirred under a slight vacuum (ca 150mm. Hg) at room temperature for 15 minutes. n-Propyl iodide (0.9g.) was added to the resulting clear solution, and the mixture stirred at room temperature overnight. The solution was added to water (300ml.) and extracted with ethyl acetate (3 × 40ml.). The combined extracts were washed with a saturated solution of sodium chloride (30ml.), dried ($MgSO_4$), and then evaporated in vacuo. The yellow oil thus obtained was treated with tetrachloroethylene (100ml.) and the solution evaporated in vacuo. This process was then replaced with ethanol (50ml.) to give ethyl 1-(7chloroquinazolin-4-yl)-2-methyl-5-n-propoxyindol-3-ylacetate as a stiff yellow syrup [NMR: 2-$CH_3$ at 7.65τ; pure by TLC (systems A and D)].

In a similar manner, but using methyl iodide, there was obtained ethyl 1-(7-chloroquinazolin-4-yl)-5-methoxy-2-methylindol-3-ylacetate as a yellow solid, m.p. 103°105° C. [NMR: 5-$OCH_3$ at 6.2τ; pure by TLC (systems A and C)].

The 5-hydroxyindole derivative used as a starting material was obtained as follows:

A solution of ethyl 5-benzyloxy-1-(7-chloroquinazolin-4-yl)-2-methylindol-3-ylacetate (1.5g) in glacial acetic acid (5ml.) was treated with a 50% w/v solution of hydrogen bromide in glacial acetic acid (5ml.). The resulting dark red solution was stirred at room temperature for 10 minutes and then neutralised by the addition to a mixture of saturated sodium acetate solution (50ml.) and water (150ml.). The mixture was extracted with ethyl acetate (3 × 50ml.) and the extracts washed successively with water (2 × 40ml.), saturated sodium hydrogen carbonate solution (2 × 40ml.), water (40ml.) and then saturated sodium chloride solution (40ml.). After drying ($MgSO_4$), the extracts gave on evaporation in vacuo a yellow-brown oil. Purification by chromatography on silica gel (200g.) in a mixture of 50% v/v ether and 50% v/v petroleum ether (b.p 40°–60° C.), gave ethyl 1-(7-chloroquinazolin-4-yl)-5-hydroxy-2-methylindol-3-ylacetate as a pale yellow glass [NMR: 2-$CH_3$ at 7.7τ; pure by TLC (systems A, C and D)].

The ethyl 5-benzyloxy-1-(7-chloroquinazolin-4-yl)-2-methylindol-3-ylacetate used as starting material was obtained as a yellow syrup [NMR: 5—$OCH_2$ at 6.25τ; pure by TLc (systems A and C)] from the corresponding acetic acid in an analogous manner to that described in Example 31.

The 5-benzyloxy-1-(7-chloroquinazolin-4-yl)-2-methylindol-3-ylacetic acid used as starting material was obtained as a yellow solid, m.p. 97°–99° C. (decomposition) from acetaldehyde $N^1$-(7-chloroquinazolin-4-yl)-p-benzyloxyphenylhydrazone hydrochloride by an analogous procedure to that described in Example 18.

EXAMPLE 35

A mixture of acetaldehyde N[1] -(7chloroquinazolin-4-yl)-p-methoxyphenylhydrazone hydrochloride (25g.) and laevulinic acid (50g.) in acetic acid (120ml.) was heated under reflux for 1–2 hours. The dark red mixture was then added to water (1.5 l.). The solid obtained was separated by filtration and dissolved in a mixture of water (50ml.) and 5N-aqueous ammonium hydroxide solution (50ml.). The solution was extracted with ether (3 × 50ml.) and the aqueous layer acidified with acetic acid to pH4. The mixture was then extracted with ethyl acetate (3 × 50ml.) and the extracts washed with water (30ml.) and then with saturated sodium chloride solution (30ml.) before being dried ($MgSO_4$). Evaporation of the solvent gave a dark brown syrup which crystallised on addition of methanol (40ml.) to give 1-(7-chloroquinazolin-4-yl)5-methoxy-2-methylindol-3-ylacetic acid as a yellow solid, m.p. 205°–208° C.

EXAMPLE 36

In a similar manner to that described in Example 18, (but the ammonium salt was not isolated in every case) the following compounds were obtained from the appropriate substituted phenylhydrazone:

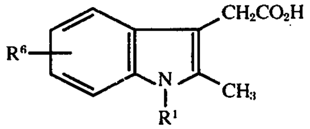

| $R^1$ | $R^6$ | Characteristic properties |
|---|---|---|
| 7-chloroquinazolin-4-yl | 5-OEt | m.p.120° C. (¼ $H_2O$) |
| 7-chloroquinazolin-4-yl | 5-Et | m.p.108–109° C. (½ $H_2O$) |
| 6,8-dibromoquinazolin-4-yl | 5-OMe | m.p.123–130° C. ($H_2O$) |
| 7-chloro-2-methyl-quinazolin-4-yl | 5-OMe | m.p.103–108° C. (¼ $H_2O$) |
| 7-chloroquinazolin-4-yl | 5-t-Bu | m.p.120–122° C. |
| quinazolin-4-yl | 5-methyl | m.p.212–216° C. |
| 7-chloroquinazolin-4-yl | 5,6-ethylene-dioxy | m.p.128–130° C. |
| 7-chloroquinazolin-4-yl | 4,6-dimethyl | m.p.117° C. |
| 7-chloroquinazolin-4-yl | mixture of 4- and 6-OMe | m.p.94–98° C. |
| 7-chloroquinazolin-4-yl | mixture of 4,5- and 5,6-diMe | m.p.114–118° C. |
| 7-chloroquinazolin-4-yl | 5-Br | m.p.95–100° C. (½ $H_2O$) |
| 5,7-dichloroquinazolin-4-yl | 5-OMe | m.p.130–135° C. |
| 7-chloroquinazolin-4-yl | 5-F | m.p.99–100° C. ($H_2O$) |
| 7-chloroquinazolin-4-yl | 5,6-methylene-dioxy | m.p.105–108° C. ($H_2O$) |
| 7-chloroquinazolin-4-yl | 5-Cl | m.p.213–217° C. |
| 2-methylquinazolin-4-yl | 5-F | pure by TLC (System E*); NMR:2-$CH_3$ at 7.80τ. |
| 2-isopropylquinazolin-4-yl | 5-OMe | pure by TLC (Systems A, C and E); NMR:2-i-Pr at 8.60 and 8.68τ. |
| 2-methylquinazolin-4-yl | 5-Me | m.p.95–100° C. ($H_2O$) |
| 2-ethylquinazolin-4-yl | 5-OMe | pure by TLC (Systems C and E); NMR:—$OCH_3$ at 6.18τ. |

*Chloroform 95 parts, methanol 4 parts, formic acid 1 part on silica gel; hereinafter referred to as System E.

In an analogous manner there were obtained α-[1-(7-chloroquinazolin-4-yl)-5-methoxy-2-methylindol-3-yl]isobutyric acid, m.p. 105°–107° C., and α-[1-(7-chloroquinazolin-4-yl)-2,5-dimethylindol-3-yl]propionic acid, m.p. 98°–102° C. (monohydrate), from the appropriate starting materials.

The following hydrazone derivatives, which were used as starting materials in this Example, were prepared in a similar manner to that described in Example 18:

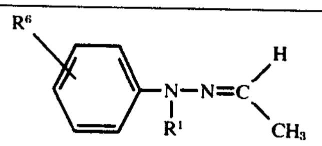

| $R^1$ | $R^6$ | Characteristic properties |
|---|---|---|
| 7-chloroquinazolin-4-yl | 4-OEt | m.p.192–194° C. (dec.) (hydrochloride) |
| 7-chloroquinazolin-4-yl | 4-Et | m.p.190–191° C. (dec.) (hydrochloride) |
| 6,8-dibromoquinazolin-4-yl | 4-OMe | m.p.113–115° C. (dec.) (hydrochloride) |
| 7-chloro-2-methyl-quinazolin-4-yl | 4-OMe | m.p.174–175° C. (dec.) (hydrochloride) |
| 7-chloroquinazolin-4-yl | 4-t-Bu | pure by TLC (Systems A and C); NMR: t-Bu at 8.65τ |
| 7-chloroquinazolin-4-yl | 3,4-ethylene-dioxy | m.p.203–206° C. (dec.) (hydrochloride) |
| 7-chloroquinazolin-4-yl | 3,5-dimethyl | glass; NMR:3,5-di-$CH_3$ at 7.55τ; pure by TLC (System C) |
| 7-chloroquinazolin-4-yl | 3-OMe | m.p.97–101° C. |
| 7-chloroquinazolin-4-yl) | 3,4-dimethyl | m.p.205–206° C. (dec.) (hydrochloride) |
| 7-chloroquinazolin-4-yl | 4-Br | m.p.175–178° C. (dec.) |
| 5,7-dichloroquinazolin-4-yl | 4-OMe | glass; NMR:—$OCH_3$ at 6.2τ; pure by TLC (Systems A and D) |
| 7-chloroquinazolin-4-yl | 4-F | m.p.198–200° C. (dec.) (hydrochloride) |
| 7-chloroquinazolin-4-yl | 3,4-methylene-dioxy | m.p.209–210° C. (dec.) (hydrochloride) |
| 7-chloroquinazolin-4-yl | 4-Cl | m.p.200–206° C. (dec.) (hydrochloride) |
| 2-methylquinazolin-4-yl | 4-F | syrup; NMR:—$CH_3$ at 7.2τ; pure by TLC (Systems A and C) |
| 2-isopropylquinazolin-4-yl | 4-OMe | syrup; NMR:—$CH_3$, doublet at 8.9τ; pure by TLC (Systems A and D) |
| 2-methylquinazolin-4-yl | 4-Me | syrup; NMR:4-$CH_3$ at 7.8τ; pure by TLC (System A) |
| 2-ethylquinazolin-4-yl | 4-OMe | syrup; NMR:—$OCH_3$ at 6.1τ; pure by TLC (Systems A and C) |
| quinazolin-4-yl | 4-Me | syrup: NMR:4-$CH_3$ at 7.85τ; pure by TLC (Systems A and C) |

EXAMPLE 37.

A solution of methyl 1-(7-aminoquinazolin-4-yl)-5-methoxy-2-methylindol-3-ylacetate (0.5g.) in acetic acid (12 ml.) was treated with concentrated hydrochloric acid (1.5 ml.). The solution obtained was stirred at 0°–5° C during the addition, over 15 minutes, of a solution of sodium nitrite (0.15g.) in water (2 ml.). The dark red solution was added dropwise to a solution of cuprous chloride (0.2g.) in concentrated hydrochloric acid (5ml.) kept at room temperature. The mixture was then stirred for 1 hr. before addition of sufficient sodium acetate to adjust the pH of the mixture to 4–5. The mixture was then concentrated in vacuo and the residue treated with water (100ml.) and ethyl acetate (50ml.). The aqueous layer was extracted with ethyl acetate (2 × 30ml.) and the extracts washed with saturated sodium hydrogen carbonate solution (2 × 30ml.). After being washed with water (30ml.) and dried($Na_2SO_4$), evaporation of the extracts in vacuo gave an oil, which slowly solidified to give methyl 1-(7-chloroquinazolin-4-yl)-5-methoxy-2-methyl-indol-3-ylacetate as a yellow solid, m.p. 111°–114° C.

The amino-derivative used as starting material was obtained as follows:

A solution of methyl 5-methoxy-2-methyl-1-(7-nitroquinazolin-4-yl)indol-3-ylacetate (2.0g.) in ethanol (80ml.; dried over sodium alumino-silicate) was treated with palladised charcoal (0.5g.; 10% w/w) and the mixture hydrogenated at atmospheric pressure. After the uptake of the theoretical amount of hydrogen, the catalyst was separated by filtration through a Celite pad. Evaporation of the ethanol gave a red syrup which was purified by chromatography on silica gel (150g.). The less polar by-products were removed by elution with ether. Elution with methanol then gave methyl 1-(7-aminoquinazolin-4-yl)-5-methoxy-2-methylindol-3-ylacetate as an orange glass having a satisfactory NMR spectrum (5—$OCH_3$ at 6.15 τ) and shown to be pure by TLC (system C).

The methyl 5-methoxy-2-methyl-1-(7-nitroquinazolin-4-yl)indol-3-ylacetate used as starting material was obtained as a red solid, m.p. 179°–181° C., from the corresponding indoline derivative as described in Example 11. Methyl 5-methoxy-2-methyl-1-(7- nitroquinazolin-4-yl-)-indolin-3-ylacetate was obtained as a red glass [NMR:5-$OCH_3$ at 6.15 $\tau$; pure by TLC (systems A and C)] in a similar manner to that described in Example 4 for the preparation of ethyl 1-quinazolin-4-ylindolin-3-ylacetate.

EXAMPLE 38.

In an analogous manner to that described in Example 16, there was obtained methyl 1-(benzoxazol-2-yl)-5-methoxy-2-methylindol-3-ylacetate, m.p. 125°–126° C., from the appropriate starting materials.

EXAMPLE 39.

In a similar manner to that described in Example 18, 1-(7-chloroquinazolin-4-yl)-5-methoxy-2-methylindol-3-ylacetic acid was prepared from acetone N[1]-(7-chloroquinazolin-4-yl)-p-methoxyphenylhydrazone hydrochloride and laevulinic acid, and it was also prepared from benzaldehyde N[1]-(7-chloroquinazolin-4-yl)-p-methoxyphenylhydrazone hydrochloride and laevulinic acid.

The starting materials were obtained as described in Example 18 for acetaldehyde N[1]-(7-chloroquinazolin-4-yl)-p-methoxyphenylhydrazone hydrochloride. Thus, from acetone p-methoxyphenylhydrazone and 4,7-dichloroquinazoline, there was obtained acetone N[1]-(7-chloroquinazolin-4-yl)-p-methoxyphenylhydrazone hydrochloride [this compound was unstable; the free base was shown to be pure by TLC (system C) when first isolated, but it decomposed on keeping] and from benzaldehyde p-methoxyphenylhydrazone and 4,7-dichloroquinazoline, there was obtained benzaldehyde N[1]-(7-chloroquinazolin-4-yl)-p-methoxyphenylhydrazone hydrochloride, m.p. 227°–228° C.

EXAMPLE 40

A mixture of 1-(7-chloroquinazolin-4-yl)-p-methoxyphenylhydrazine (2.0g.) and laevulinic acid (8.0g.) was heated at 90°–95° C for 4hrs. The dark red mixture was poured into water. The yellow precipitate was collected by filtration, dissolved in a mixture of 2N-aqueous ammonia solution (25ml.) and water (25ml.) and filtered. The filtrate was washed with ether (2 × 30ml.), and the aqueous layer acidified with acetic acid to pH 4 to give 1-(7-chloroquinazolin-4-yl)-5-methoxy-2-methylindol-3-ylacetic acid hemi-hydrate, m.p. 94°–96° C.(dec.) The hemi-hydrate (1.8g.) was dissolved in ethyl acetate (50ml.), and the solution dried ($MgSO_4$) and evaporated in vacuo. The resulting yellow glass was treated with methanol (10ml.) to give anhydrous 1-(7-chloroquinazolin-4-yl)-5-methoxy-2-methylindol-3-ylacetic acid, m.p. 206°–208° C.

In a similar manner, but starting with the appropriate oxo-compound, there were obtained the following derivatives:

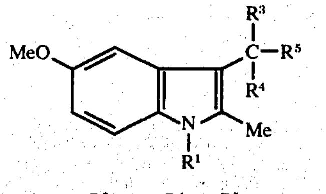

| $R^1$ | $R^3$ | $R^4$ | $R^5$ | m.p. |
|---|---|---|---|---|
| 7-chloroquinazolin-4-yl | H | H | $CO_2Me$ | 112–114° C |
| 7-chloroquinazolin-4-yl | H | H | $CH_2OH$ | 148–150° C |
| 7-chloroquinazolin-4-yl | Me | H | $CO_2H$ | 110–112° C |
| 7-chloroquinazolin-4-yl | Me | Me | $CO_2H$ | 105–107° C |

-continued

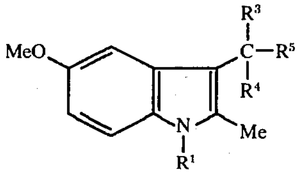

| $R^1$ | $R^3$ | $R^4$ | $R^5$ | m.p. |
|---|---|---|---|---|
| 7-chloroquinazolin-4-yl | H | H | $CONH_2$ | 197–198° C |

The starting material was obtained by the following two methods:

(i) A solution of 4,7-chloroquinazoline (1.0g.) and p-methoxyphenylhydrazine (0.7g.) in 1,2-dimethoxyethane (25ml.; dried over sodium alumino-silicate) was heated under reflux for 1 hr. The resulting red mixture was concentrated in vacuo to give a sticky residue, to which was added water (50ml.) and ethyl acetate (50ml.). The aqueous layer was extracted with ethyl acetate (2 × 30ml.). The combined extracts were washed with water, dried ($Na_2SO_4$) and evaporated in vacuo. The resultant red syrup was purified by chromatography on silica (MFC,130g.) in an increasing gradient of ether in petroleum ether (b.p. 40°–60° C.) (polarity increased by incremental addition of 20% v/v ether), to give from the ether rich fractions, N[1]-(7-chloroquinazolin-4-yl)-p-methoxyphenylhydrazine, as a yellow solid, m.p. 125°–127° C.

(ii) A suspension of acetaldehyde N[1]-(7-chloroquinazolin-4-yl)-p-methoxyphenylhydrazone hydrochloride (15.0g.) in ethanol (120ml.; dried over magnesium ethoxide) was cooled and stirred at 5°–10° C for 3 hrs. during the passage of dry hydrogen chloride. The mixture was then left at 0°–5° C. for 3 days before separation by filtration. The solid was washed with dry ether (10ml.), and then dissolved in a mixture of water (30ml.), saturated sodium acetate solution (5ml.) and ethyl acetate (25ml.). The aqueous layer was extracted with more ethyl acetate (2 × 15ml.), and the extracts washed with water (20ml.), dried ($Na_2SO_4$) and evaporated to give N[1]-(7-chloroquinazolin-4-yl)-p-methoxyphenylhydrazine, m.p. 124°–127° C.

EXAMPLE 41

In an analogous manner to that described in Example 11 there was obtained methyl 1-(2-methoxyquinazolin-4-yl)-5-methoxy-2-methylindol-3-ylacetate, m.p. 152°–154° C., from the appropriate starting material.

The starting material was prepared as follows:

A mixture of 2,4-dichloroquinazoline (3.2g.), ethyl 5-methoxy-2-methylindolin-3-ylacetate (4.0g.) and triethylamine (2.23ml; dried over potassium hydroxide pellets) in dry 1,2-dimethoxyethane (50ml.) was heated under reflux for 30 mins. The mixture was evaporated in vacuo, and to the residue was added water (100ml.) and ethyl acetate (50ml.). The aqueous layer was separated and extracted with ethyl acetate (2 × 30ml.), and the extracts were washed with water (30ml.), dried($MgSO_4$) and evaporated. The residual syrup slowly crystallised to give ethyl 1-(2-chloroquinazolin-4-yl)-5-methoxy-2-methylindolin-3-ylacetate, m.p. 111°–112° C. This indoline ester (3.6g.) was added to a solution of sodium (0.5g.) in methanol (50ml.; dried over magnesium methoxide), and the resulting solution was heated under reflux for 18 hrs.

After removal of methanol in vacuo, the mixture was added to water (50ml.) and acidified with acetic acid to give 1-(2-methoxyquinazolin-4-yl)-5-methoxy-2-methylindolin-3-ylacetic acid hemihydrate, m.p. 115°–120° C. This acid (3.0g.) was dissolved in dry methanol (40ml.) containing concentrated sulphuric acid (0.1ml.), and the mixture was heated under reflux for 5 hrs. Saturated sodium acetate solution (2ml.) was added, and the mixture was evaporated in vacuo. The residue was partitioned between water (50ml.) and ether (40ml.). After separation, the aqueous layer was extracted with ether (2 × 20ml.). The ether extracts were washed successively with saturated sodium hydrogen carbonate solution (20ml.) and water (20ml.), dried ($Na_2SO_4$), and evaporated to give methyl 1-(2-methoxyquinazolin-4-yl)-5-methoxy-2-methhylindolin-3-ylacetate as a dark yellow syrup [pure by TLC (system A); NMR: 5—$OCH_3$ at 6.3τ; 2—$OCH_3$ at 6.15τ].

EXAMPLE 42.

To a solution of 1-(7-chloroquinazolin-4-yl)-5-methoxy-2-methylindol-3-ylacetic acid (1.0g.) in dry methanol (50ml.) was added freshly distilled boron trifluoride etherate (0.5ml.), and the dark red solution was heated under reflux for 30 mins. To the solution was added saturated sodium acetate solution (5ml.), and the mixture was concentrated in vacuo. The residual mixture was shaken with a mixture of water (50ml.) and chloroform (30ml.). The aqueous layer was separated and extracted with further chloroform (2 × 20 ml.), and the combined extracts were washed successively with saturated sodium hydrogen carbonate solution (2 × 20ml.), water (10ml.) and saturated sodium chloride solution (15ml.). After drying, the extracts were evaporated to give methyl 1(7-chloroquinazolin-4-yl)-5-methoxy-2-methylindol-3-ylacetate, m.p. 111°–113° C.

In a similar manner, but starting with butan-1-ol, there was obtained n-butyl 1-(7-chloroquinazolin-4-yl)-5-methoxy-2-methylindol-3-ylacetate, as a yellow syrup [pure by TLC (systems A and C); NMR: 5—$OCH_3$ at 6.2τ]. Ethyl 1-(7-chloroquinazolin-4-yl)-5-methoxy-2-methylindol-3-ylacetate was obtained similarly as a pale yellow solid, m.p. 103°–105° C.

EXAMPLE 43.

To a solution of anhydrous 1-(7-chloroquinazolin-4-yl)-5-methoxy-2-methylindol-3-ylacetic acid (1.0g.) in ethanol-free chloroform (30 ml; dried over calcium chloride) was added a solution of thionyl chloride (0.19 ml.) in chloroform (2ml). The resulting dark red solution was stirred at room temperature for 30 mins., and then methanol (20 ml.) was added. The mixture was heated under reflux for 30 mins., saturated sodium acetate solution (2 ml.) was added, and the mixture was concentrated in vacuo. Water (30 ml.) was added to the residue and the mixture was extracted with ether (3 × 30 ml.). The ether extracts were washed successively with saturated sodium hydrogen carbonate solution (30 ml.) and water (30 ml.), and dried ($Na_2SO_4$). Evaporation of the solvent gave a dark yellow oil, which slowly crystallised to give methyl 1-(7-chloroquinazolin-4-yl)-5-methoxy-2-methylindol-3-ylacetate, m.p. 112°–114° C.

In a similar manner, but using ethanol, there was obtained ethyl 1-(7-chloroquinazolin-4-yl)-5-methoxy-2-methylindol-3-ylacetate as a thick syrup of satisfactory purity by TLC (systems A and C) and by NMR ($OCH_3$ at 6.2τ). This slowly crystallised to give a yellow solid of m.p. 103°–105° C.

EXAMPLE 44.

A solution of 1-(7-chloroquinazolin-4-yl)-5-methoxy-2-methylindol-3-ylacetic acid (1.0.g.) in ammonia solution (1 ml.; specific gravity 0.88) and carbon dioxide-free water (20 ml.) was evaporated to dryness in vacuo to give the corresponding ammonium salt as a yellow amorphous solid.

The ammonium salt was dissolved in carbon dioxide-free water (10 ml.), and to the resulting clear yellow solution was added a solution of aluminum nitrate monohydrate (0.33g.) in water (10.ml.). The yellow precipitate which formed was separated by filtration, washed with water (10ml.), and dried over phosphorus pentoxide in vacuo to give aluminium 1-(7-chloroquinazolin-4-yl)-5-methoxy-2-methylindol-3-ylacetate monohydrate, as a yellow solid of m.p. 204°–208° C.(dec.)

In a similar manner there was obtained the calcium salt [1½$H_2O$; m.p. 203°–205° C.(dec.)] and the magnesium salt [1½$H_2O$; m.p. 198°–201° C.(dec.)] from calcium chloride and magnesium sulphate respectively.

EXAMPLE 45.

1-(7-chloroquinol-4-yl)-5-methoxy-2-methylindol-3-ylacetic acid (200 g.) was thoroughly mixed with lactose (400 g.) and 10% w/v aqueous gelatin solution (9 g.), and the mixture was then granulated. Maize starch (35 g.) was mixed with the granules, followed by magnesium stearate (6 g.), and the mixture was compressed into tablets containing 50,100 or 200 mg. of the active ingredient.

EXAMPLE 46

A mixture of laevulinic acid (7 g.), acetaldehyde $N^1$-(2-methylthioquinazolin-4-yl)-p-methoxyphenylhydrazone (3.5 g.) and a saturated solution of hydrogen chloride in ether (2 ml.) was heated at 95° – 100° C. for 22 hours. The mixture was poured into water (300 ml.), and the precipitated brown solid was collected by filtration and dissolved in chloroform (100 ml.). The solution was filtered and the filtrate was extracted with 2 N- ammonia solution (4 × 50 ml.). The extracts were combined and acidified to pH3 with glacial acetic acid. The mixture was filtered, and the solid crystallised from methanol to give 5-methoxy-2-methyl-1-(2-methylthioquinazolin-4-yl)indol-3-ylacetic acid, as a pale yellow crystalline solid, m.p. 175°–178° C.

In a similar manner, starting from the corresponding acetaldehyde hydrazone (or its hydrochloride), there were obtained the following compounds

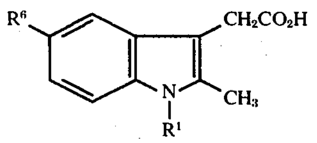

| $R^1$ | $R^6$ | Characteristic properties |
|---|---|---|
| 2-ethylthioquinazolin-4-yl | methoxy | m.p. 214–215° C. |
| 2-methylthioquinazolin-4-yl | methyl | m.p. 208–211° C. |
| 2-methylthioquinazolin-4-yl | hydrogen | m.p. 205–207° C. |
| 7-chloroquinazolin-4-yl | hydrogen | m.p. 202–205° C. |
| 2-methylquinazolin-4-yl | hydrogen | m.p. 95–98° C (hemihydrate) |
| quinazolin-4-yl | methyl | m.p. 212–216° C. |

-continued

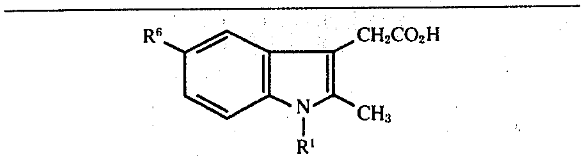

| $R^1$ | $R^6$ | Characteristic properties |
|---|---|---|
| 6-chloro-2-methylquinazolin-4-yl | methoxy | m.p. 115–120° C. (hemihydrate) |

The following acetaldehyde hydrazone derivatives used as starting materials for the preparation of the indole derivatives described in this example were prepared in a similar manner to that described in Example 18, except that if necessary, they were purified by chromatography on silica gel using as eluant, an increasing gradient of ether in petroleum ether (b.p. 40°–60° C.).

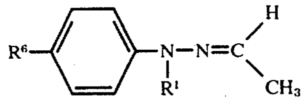

| $R^1$ | $R^6$ | Characteristic properties |
|---|---|---|
| 2-methylthioquinazolin-4-yl | methoxy | m.p. 195–198° C. (hydrochloride) |
| 2-ethylthioquinazolin-4-yl | methoxy | NMR: $-OCH_3$ at 6.15τ; pure by TLC (Systems A and D). |
| 2-methylthioquinazolin-4-yl | methyl | NMR: 4-$CH_3$ at 7.7τ, $-SCH_3$ at 7.45τ; pure by TLC (Systems A and D). |
| 7-chloroquinazolin-4-yl | hydrogen | m.p. 218–220° C. |
| 2-methylquinazolin-4-yl | hydrogen | m.p. 115–120° C. (decomposition) |
| quinazolin-4-yl | methyl | NMR: 4-$CH_3$ at 7.8τ |
| 6-chloro-2-methylquinazolin-4-yl) | methoxy | m.p. 207–210° C. (decomposition) |

EXAMPLE 47

In an analogous manner to that described in Example 11, methyl 5-methoxy-2-methyl-1-(2-methylthioquinazolin-4-yl)indol-3-ylacetate was obtained as a pale yellow solid, m.p. 151°–153° C. by reaction of 2,3-dichloro-5,6-dicyano-1,4-benzoquinone with methyl 5-methoxy-2-methyl-1-(2-methylthioquinazolin-4-yl)indolin-3-ylacetate, itself obtained as a bright yellow syrup [NMR, indoline 2—$CH_3$: doublet at 8.84τ, $SCH_3$: singlet at 7.8τ; pure by TLC (Systems A,D)] in a similar manner to that described for ethyl 1-quinazolin-4-ylindolin-3-ylacetate in Example 4.

EXAMPLE 48

In an analogous manner to that described in Example 29, 1-(4,6-dimethoxypyrimidin-2-yl)-5-methoxy-2-methylindol-3-ylacetic acid was obtained as a crystalline solid, m.p. 213°–215° C. (decomposition), from 1-(4,6-dichloropyrimidin-2-yl)-5-methoxy-2-methylindol-3-ylacetic acid, m.p. 228°–229° C.

The above starting material was obtained from N-(p-methoxyphenyl)-N(4,6-dichloropyrimidin-2-yl)hydrazine in a similar manner to that described in Example 2 for 1-(2,6-dichloropyrimidin-4-yl)-2-methylindol-3-ylacetic acid. The hydrazine derivative used as starting material was obtained as follows:

A mixture of p-methoxyphenylhydrazine (59 g.), 2,4,6-trichloropyrimidine (78.5 g.), and a solution of anhydrous sodium acetate (63 g.) in a mixture of water (260 ml.) and ethanol (1200 ml.) was shaken at room temperature for 2 hours. The crystalline precipitate which had formed was collected by filtration, washed with ethanol (50 ml.) and recrystallised from a mixture of chloroform (200 ml.) and ethanol (800 ml.) to give N-(p-methoxyphenyl)-N-(2,6-dichloropyrimidin-4-yl)hydrazine as a pale yellow solid, m.p. 156°–158° C. From the crystallisation mother liquors there was obtained, after chromatography on silica gel (300 g.) using a mixture containing equal parts by volume of ether and petroleum ether (b.p. 40° C.), N-(p-methoxyphenyl)-N-(4,6-dichloropyrimidin-2-ylhydrazine as a pale yellow solid, m.p. 113°–115° C.

What we claim is:

1. A pharmaceutical composition for use in providing an analgesic or anti-inflammatory effect comprising an effective amount of a compound of the formula:

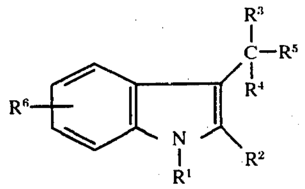

I wherein $R^1$ is a quinazolinyl radical or a quinazolinyl radical bearing not more than two substituents selected from $C_{1-5}$-alkyl, $C_{1-5}$-alkoxy, $C_{1-5}$-alkylthio, amino, halogen, trifluoromethyl, trichloromethyl and phenyl substituents, the quinazolinyl radical being linked to the nitrogen atom of the indole nucleus through position 2 or 4 of the quinazolinyl radical; and $R^2$ stands for hydrogen or a $C_{1-3}$-alkyl radical; and $R^3$ and $R^4$, which may be the same or different, stand for hydrogen or a methyl radical; and $R^5$ is a radical of the formula -$COR^7$ wherein $R^7$ stands for a hydroxy, $C_{1-5}$-alkoxy, benzyloxy, phenoxy, di-$C_{1-5}$-alkylamino-$C_{1-5}$-alkoxy, ($C_{3-6}$-cycloalkyl)methoxy, amino, $C_{1-5}$-alkylamino or di-$C_{1-5}$-alkylamino and $R^6$ stands for hydrogen or a methylenedioxy or ethylenedioxy radical or not more than two substituents selected from $C_{1-5}$-alkoxy, $C_{1-5}$-alkyl, cycloalkyl of not more than 5 carbon atoms, and di-$C_{1-5}$-alkylamino radicals and halogen atoms; or a pharmaceutically-acceptable salt thereof, and an inert pharmaceutically-acceptable carrier therefor.

2. A pharmaceutical composition as claimed in claim 1 wherein the compound of Formula I is 5-methoxy-2-methyl-1-(2-methylquinazolin-4-yl)-indol-3-ylacetic acid or a pharmaceutically-acceptable salt thereof.

3. A pharmaceutical composition as claimed in claim 1 wherein the compound of Formula I is 1-(7-chloroquinazolin-4-yl)-2,5-dimethylindol-3-ylacetic acid or a pharmaceutically-acceptable salt thereof.

4. A pharmaceutical composition as claimed in claim 1 wherein the compound of Formula I is 1-(7-chloroquinazolin-4-yl)-5-fluoro-2-methylindol-3-ylacetic acid or a pharmaceutically-acceptable salt thereof.

5. A pharmaceutical composition as claimed in claim 1 wherein the compound of Formula I is methyl 1-(7-chloroquinazolin-4-yl)-5-methoxy-2-methylindol-3- ylacetate or a pharmaceutically-acceptable salt thereof.

6. A pharmaceutical composition as claimed in claim 1 wherein the compound of formula I is 1-(7-chloroquinazolin-4-yl)-5-methoxy-2-methylindol-3-ylacetic acid or pharmaceutically-acceptable salt thereof.

7. A method of producing an anti-inflammatory effect in a host requiring such treatment which comprises administering to said host an effective amount of a compound of the Formula I:

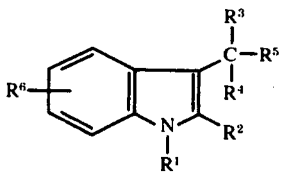

wherein $R^1$ is a quinazolinyl radical or a quinazolinyl radical bearing not more than two substituents selected from $C_{1-5}$-alkyl, $C_{1-5}$-alkoxy, $C_{1-5}$-alkylthio, amino, halogen, trifluoromethyl, trichloromethyl and phenyl substituents, the quinazolinyl radical being linked to the nitrogen atom of the indole nucleus through position 2 or 4 of the quinazolinyl radical; and $R^2$ stands for hydrogen or a $C_{1-3}$-alkyl radical; and $R^3$ and $R^4$, which may be the same or different, stand for hydrogen or a methyl radical; and $R^5$ is a radical of the formula —$COR^7$ wherein $R^7$ stands for a hydroxy, $C_{1-5}$-alkoxy, benzyloxy, phenoxy, di-$C_{1-5}$-alkylamino-$C_{1-5}$-alkoxy, ($C_{3-6}$-cycloalkyl)methoxy, amino, $C_{1-5}$-alkylamino or di-$C_{1-5}$-alkylamino and $R^6$ stands for hydrogen or a methylenedioxy or ethylenedioxy radical or not more than two substituents selected from $C_{1-5}$-alkoxy, $C_{1-5}$-alkyl, cycloalkyl of not more than 5 carbon atoms, and di-$C_{1-5}$-alkylamino radicals and halogen atoms; or a pharmaceutically-acceptable salt thereof.

8. A method of producing an analgesic effect in a host requiring such treatment which comprises administering to said host an effective amount of a compound of the formula I:

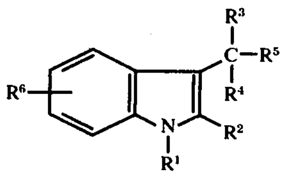

wherein $R^1$ is a quinazolinyl radical or a quinazolinyl radical bearing not more than two substituents selected from $C_{1-5}$-alkyl, $C_{1-5}$-alkoxy, $C_{1-5}$-alkylthio, amino, halogen, trifluoromethyl, trichloromethyl and phenyl substituents, the quinazolinyl radical being linked to the nitrogen atom of the indole nucleus through position 2 or 4 of the quinazolinyl radical; and $R^2$ stands for hydrogen or a $C_{1-3}$-alkyl radical; and $R^3$ and $R^4$, which may be the same or different, stand for hydrogen or a methyl radical; and $R^5$ is a radical of the formula —$COR^7$ wherein $R^7$ stands for a hydroxy, $C_{1-5}$-alkoxy, benzyloxy, phenoxy, di-$C_{1-5}$-alkylamino-$C_{1-5}$-alkoxy, ($C_{3-6}$-cycloalkyl)methoxy, amino, $C_{1-5}$-alkylamino or di-$C_{1-5}$-alkylamino and $R^6$ stands for hydrogen or a methylenedioxy or ethylenedioxy radical or not more than two substituents selected from $C_{1-5}$-alkoxy, $C_{1-5}$-alkyl, cycloalkyl of not more than 5 carbon atoms, and di-$C_{1-5}$-alkylamino radicals and halogen atoms; or a pharmaceutically-acceptable salt thereof.

* * * * *